US011739385B2

(12) United States Patent
Treon

(10) Patent No.: US 11,739,385 B2
(45) Date of Patent: *Aug. 29, 2023

(54) DISCOVERY OF A SOMATIC MUTATION IN MYD88 GENE IN LYMPHOPLASMACYTIC LYMPHOMA

(71) Applicant: Dana-Farber Cancer Institute, Inc., Boston, MA (US)

(72) Inventor: Steven P. Treon, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 465 days.

This patent is subject to a terminal disclaimer.

(21) Appl. No.: 16/580,523

(22) Filed: Sep. 24, 2019

(65) Prior Publication Data

US 2020/0149114 A1 May 14, 2020

Related U.S. Application Data

(63) Continuation of application No. 14/128,241, filed as application No. PCT/US2012/044956 on Jun. 29, 2012, now Pat. No. 10,465,247.

(60) Provisional application No. 61/571,657, filed on Jul. 1, 2011.

(51) Int. Cl.
*C12Q 1/68* (2018.01)
*C12Q 1/6886* (2018.01)
*A61K 45/06* (2006.01)
*A61K 31/519* (2006.01)

(52) U.S. Cl.
CPC .......... *C12Q 1/6886* (2013.01); *A61K 31/519* (2013.01); *A61K 45/06* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 10,465,247 | B2 | 11/2019 | Treon |
| 10,525,060 | B2 | 1/2020 | Treon et al. |
| 10,526,660 | B2 | 1/2020 | Treon et al. |
| 2002/0156081 | A1 | 10/2002 | Hirst et al. |
| 2004/0137489 | A1 | 7/2004 | Shaughnessy |
| 2007/0281907 | A1 | 12/2007 | Watkins |
| 2009/0156469 | A1 | 6/2009 | Ghobrial et al. |
| 2010/0009350 | A1 | 1/2010 | Chow |
| 2010/0216115 | A1 | 8/2010 | Yan et al. |
| 2012/0065201 | A1 | 3/2012 | Honigberg et al. |
| 2012/0071497 | A1 | 3/2012 | Buggy et al. |
| 2014/0249142 | A1 | 9/2014 | Treon |
| 2015/0210698 | A1 | 7/2015 | Ishikawa et al. |
| 2016/0222465 | A1 | 8/2016 | Treon et al. |
| 2016/0304958 | A1 | 10/2016 | Treon et al. |
| 2017/0333436 | A1 | 11/2017 | Treon et al. |
| 2020/0199683 | A1 | 6/2020 | Treon et al. |

FOREIGN PATENT DOCUMENTS

| CN | 107056786 A | 8/2017 |
| EP | 2 878 601 A1 | 6/2015 |
| JP | 2010-235628 | 10/2010 |
| WO | WO 2001/019829 A2 | 3/2001 |
| WO | WO 2006/067091 A1 | 6/2006 |
| WO | WO 2008/060367 A2 | 5/2008 |
| WO | WO 2011/095556 A1 | 8/2011 |
| WO | WO 2013/006443 A2 | 1/2013 |
| WO | WO 2013/071068 A2 | 5/2013 |
| WO | WO 2014/017659 A1 | 1/2014 |
| WO | 2015/038887 | 3/2015 |
| WO | WO 2017/172826 A1 | 10/2017 |
| WO | WO 2017/189999 A1 | 11/2017 |

OTHER PUBLICATIONS

Extended European Search Report for EP12807230.3 dated Feb. 2, 2015.
Extended European Search Report for EP14844516.6 dated Mar. 28, 2017.
International Preliminary Report on Patentability for PCT/US2012/044956 dated Jan. 16, 2014.
International Preliminary Report on Patentability for PCT/US2014/055386 dated Mar. 24, 2016.
International Preliminary Report on Patentability for PCT/US2014/068579 dated Jun. 16, 2016.
International Preliminary Report on Patentability for PCT/US2017/030116 dated Jun. 16, 2016.
International Search Report and Written Opinion for PCT/US2012/044956 dated Dec. 17, 2012.

(Continued)

*Primary Examiner* — Jehanne S Sitton
(74) *Attorney, Agent, or Firm* — Wolf, Greenfield & Sacks, P.C.

(57) ABSTRACT

Diagnostic assays for facilitating the diagnosis of lymphoplasmacytic lymphoma (LPL) are provided. The method comprises assessing a biological sample of the subject for the presence of a mutation at position 38182641 in chromosome 3p22.2, wherein presence of the mutation is indicative that the subject has LPL. Also, provided are targeted therapies, methods for monitoring the progression or recurrence of LPL, and a sensitive and inexpensive real-time allele specific polymerase chain reaction assay for reliable and quantitative assessments of the mutation.

15 Claims, 8 Drawing Sheets

Specification includes a Sequence Listing.

(56) References Cited

OTHER PUBLICATIONS

International Search Report and Written Opinion for PCT/US2014/055386 dated Dec. 23, 2014.
International Search Report and Written Opinion for PCT/US2014/068579 dated Mar. 3, 2015.
International Search Report and Written Opinion for PCT/US2017/030116 dated Aug. 21, 2017.
[No Author Listed] Package Insert. Campath (ALEMTUZUMAB). Millennium and ILEX Partners, LP. Date created Sep. 26, 2003;1-11.
[No Author Listed] Trademark Electronic Search System (TESS) Typed Drawing. May 21, 1991. 2nd Renewal Apr. 24, 2013. Last accessed Apr. 4, 2018.
Advani et al., Bruton tyrosine kinase inhibitor ibrutinib (PCI-32765) has significant activity in patients with relapsed/refractory B-cell malignancies. J Clin Oncol. Jan. 1, 2013;31(1):88-94. doi: 10.1200/JCO.2012.42.7906. Epub Oct. 8, 2012.
Anderson et al., Multiple myeloma, version 1.2013. J Natl Compr Canc Netw. Jan. 1, 2013;11(1):11-7.
Arcaini et al., Distinctive clinical and histological features of Waldenström's macroglobulinemia and splenic marginal zone lymphoma. Clin Lymphoma Myeloma Leuk. Feb. 2011;11(1):103-5. doi:10.3816/CLML.2011.n.020.
Argentou et al., Rapid detection of MYD88-L265P mutation by PCR-RFLP in B-cell lymphoproliferative disorders. Leukemia. Feb. 2014;28(2):447-9. doi: 10.1038/leu.2013.294. Epub Oct. 18, 2013.
Balabanian et al., WHIM syndromes with different genetic anomalies are accounted for by impaired CXCR4 desensitization to CXCL12. Blood. Mar. 15, 2005;105(6):2449-57. Epub Nov. 9, 2004.
Bam et al., Role of Bruton's tyrosine kinase in myeloma cell migration and induction of bone disease. Am J Hematol. Jun. 2013;88(6):463-71. doi: 10.1002/ajh.23433. Epub Mar. 28, 2013.
Baxter et al., Acquired mutation of the tyrosine kinase JAK2 in human myeloproliferative disorders. Lancet. Mar. 19-25, 2005;365(9464):1054-61.
Berger et al., Clinicopathologic features of Waldenstrom's macroglobulinemia and marginal zone lymphoma: are they distinct or the same entity? Clin Lymphoma. Mar. 2005;5(4):220-4. Abstract.
Bergsagel et al., Comprehensive identification of somatic mutations in chronic lymphocytic leukemia. Cancer Cell. Jul. 12, 2011;20(1):5-7. doi:10.1016/j.ccr.2011.06.023.
Bohers et al., Targetable activating mutations are very frequent in GCB and ABC diffuse large B-cell lymphoma. Genes Chromosomes Cancer. Feb. 2014;53(2):144-53. doi:10.1002/gcc.22126. Epub Nov. 5, 2013.
Brikos et al., Mass spectrometric analysis of the endogenous type I interleukin-1 (IL-1) receptor signaling complex formed after IL-1 binding identifies IL-1RAcP, MyD88, and IRAK-4 as the stable components. Mol Cell Proteomics. Sep. 2007;6(9):1551-9. Epub May 15, 2007.
Busillo et al., Regulation of CXCR4 signaling. Biochim Biophys Acta. Apr. 2007;1768(4):952-63. Epub Nov. 10, 2006.
Busillo et al., Site-specific phosphorylation of CXCR4 is dynamically regulated by multiple kinases and results in differential modulation of CXCR4 signaling. J Biol Chem. Mar. 5, 2010;285(10):7805-17. doi: 10.1074/jbc.M109.091173. Epub Jan. 4, 2010.
Cao et al., CXCR4 WHIM-like frameshift and nonsense mutations promote ibrutinib resistance but do not supplant MYD88(L265P)-directed survival signalling in Waldenström macroglobulinaemia cells. Br J Haematol. Mar. 2015;168(5):701-7. doi: 10.1111/bjh.13200. Epub Nov. 5, 2014.
Cao et al., The WHIM-like CXCR4(S338X) somatic mutation activates AKT and ERK, and promotes resistance to ibrutinib and other agents used in the treatment of Waldenstrom's Macroglobulinemia. Leukemia. Jan. 2015;29(1):169-76. doi: 10.1038/leu.2014.187. Epub Jun. 10, 2014.
Cao et al., Whole Genome Sequencing Identifies Recurring Somatic Mutations in the C-Terminal Domain of CXCR4, Including a Gain of Function Mutation in Waldenstrom's Macroglobinemia. Blood. 2012;120: Abstract 2715.
Carnevali et al., Computational techniques for human genome resequencing using mated gapped reads. J Comput Biol. Mar. 2012;19(3):279-92. doi: 10.1089/cmb.2011.0201. Epub Dec. 16, 2011.
Chen, Treatment for Waldenstrom's macroglobulinemia. Ann Oncol. Apr. 2004;15(4):550-8.
Cheng et al., Binding of Bruton's tyrosine kinase to Fyn, Lyn, or Hck through a Src homology 3 domain-mediated interaction. Proc Natl Acad Sci U S A. Aug. 16, 1994;91(17):8152-5.
Chng et al., Gene-expression profiling of Waldenstrom macroglobulinemia reveals a phenotype more similar to chronic lymphocytic leukemia than multiple myeloma. Blood. Oct. 15, 2006;108(8):2755-63. Epub Jun. 27, 2006.
Dasmahaptra et al., The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib. Br J. Haematol. Apr. 2013;161(1):43-56. Abstract only.
Dave et al., Molecular diagnosis of Burkitt's lymphoma. N Engl J Med. Jun. 8, 2006;354(23):2431-42.
Davies et al., Preclinical pharmacology of AZD5363, an inhibitor of AKT: pharmacodynamics, antitumor activity, and correlation of monotherapy activity with genetic background. Mol Cancer Ther. Apr. 2012;11(4):873-87. doi: 10.1158/1535-7163.MCT-11-0824-T. Epub Jan. 31, 2012.
Ditzel et al., Establishment of BCWM.1 cell line for Waldenström's macroglobulinemia with productive in vivo engraftment in SCID-hu mice. Exp Hematol. Sep. 2007;35(9):1366-75.
Dotta et al., Clinical and genetic features of Warts, Hypogammaglobulinemia, Infections and Myelokathexis (WHIM) syndrome. Curr Mol Med. Jun. 2011;11(4):317-25.
Drmanac et al., Human genome sequencing using unchained base reads on self-assembling DNA nanoarrays. Science. Jan. 1, 2010;327(5961):78-81.
Evans et al., Inhibition of Btk with CC-292 provides early pharmacodynamic assessment of activity in mice and humans. J Pharmacol Exp Ther. Aug. 2013;346(2):219-28. doi:10.1124/jpet.113.203489. Epub May 24, 2013.
Farré et al., Identification of patterns in biological sequences at the ALGGEN server: PROMO and MALGEN. Nucleic Acids Res. Jul. 1, 2003;31(13):3651-3.
Futahashi et al., Separate elements are required for ligand-dependent and -independent internalization of metastatic potentiator CXCR4. Cancer Sci. Mar. 2007;98(3):373-9.
Gachard et al., IGHV gene features and MYD88 L265P mutation separate the three marginal zone lymphoma entities and Waldenström macroglobulinemia/lymphoplasmacytic lymphomas. Leukemia. Jan. 2013;27(1):183-9. doi: 10.1038/leu.2012.257. Epub Sep. 4, 2012.
Gay et al., Assembly and localization of Toll-like receptor signalling complexes. Nat Rev Immunol. Aug. 2014;14(8):546-58. doi: 10.1038/nri3713.
Genbank Submission; NIH/NCBI, Accession No. NM_001008540. Micucci et al., Mar. 18, 2016.
Gertz et al., Waldenström's macroglobulinemia. Oncologist. 2000;5(1):63-7.
Gopal et al., PI3Kδ inhibition by idelalisib in patients with relapsed indolent lymphoma. N Engl J Med. Mar. 13, 2014;370(11):1008-18. doi: 10.1056/NEJMoa1314583. Epub Jan. 22, 2014.
Gutiérrez et al., Gene expression profiling of B lymphocytes and plasma cells from Waldenström's macroglobulinemia: comparison with expression patterns of the same cell counterparts from chronic lymphocytic leukemia, multiple myeloma and normal individuals. Leukemia. Mar. 2007;21(3):541-9. Epub Jan. 25, 2007.
Hallek et al., Signal transduction of interleukin-6 involves tyrosine phosphorylation of multiple cytosolic proteins and activation of Src-family kinases Fyn, Hck, and Lyn in multiple myeloma cell lines. Exp Hematol. Dec. 1997;25(13):1367-77.

(56) References Cited

OTHER PUBLICATIONS

Hanke et al., Discovery of a novel, potent, and Src family-selective tyrosine kinase inhibitor. Study of Lck- and FynT-dependent T cell activation. J Biol Chem. Jan. 12, 1996;271(2):695-701.

Harris et al., A revised European-American classification of lymphoid neoplasms: a proposal from the International Lymphoma Study Group. Blood. Sep. 1, 1994;84(5):1361-92.

Herman et al., Bruton tyrosine kinase represents a promising therapeutic target for treatment of chronic lymphocytic leukemia and is effectively targeted by PCI-32765. Blood. Jun. 9, 2011;117(23):6287-96. doi: 10.1182/blood-2011-01-328484. Epub Mar. 21, 2011.

Hodge et al., IL-21 in the bone marrow microenvironment contributes to IgM secretion and proliferation of malignant cells in Waldenstrom macroglobulinemia. Blood. Nov. 1, 2012;120(18):3774-82. doi: 10.1182/blood-2012-03-419440. Epub Sep. 13, 2012.

Hong et al., The Src family kinase Hck regulates mast cell activation by suppressing an inhibitory Src family kinase Lyn. Blood. Oct. 1, 2007;110(7):2511-9. Epub May 18, 2007. Erratum in: Blood. Mar. 15, 2008;111(6):3299.

Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010; 107(29):13075-80. doi: 10.1073/pnas.1004594107. Epub Jul. 6, 2010.

Hunter et al., Recurring activation mutations and somatic deletions revealed through whole genome sequencing in Waldenstrom's Macroglobulinemia. Hematol Oncol. Jun. 2013; 31(S1): Abstract 093.

Hunter et al., The genomic landscape of Waldenstrom macroglobulinemia is characterized by highly recurring MYD88 and WHIM-like CXCR4 mutations, and small somatic deletions associated with B-cell lymphomagenesis. Blood. Mar. 13, 2014;123(11):1637-46. doi:10.1182/blood-2013-09-525808. Epub Dec. 23, 2013.

Hunter et al., Use of whole genome sequencing to identify highly recurrent somatic mutations in Waldenström's macroglobulinemia. 2012 ASCO Annual Meeting. Jun. 1-Jun. 5. Chicago, Illinois: Abstract 8107.

Janz, Waldenström macroglobulinemia: clinical and immunological aspects, natural history, cell of origin, and emerging mouse models. ISRN Hematol. Sep. 9, 2013;2013:815325. doi: 10.1155/2013/815325.

Jeelall et al., Oncogenic MYD88 mutation drives Toll pathway to lymphoma. Immunol Cell Biol. Aug. 2011;89(6):659-60. doi: 10.1038/icb.2011.31. Epub Apr. 26, 2011.

Jiménez et al., MYD88 L265P is a marker highly characteristic of, but not restricted to, Waldenström's macroglobulinemia. Leukemia. Aug. 2013;27(8):1722-8. doi: 10.1038/leu.2013.62. Epub Feb. 28, 2013.

Jourdan et al., Characterization of a transitional preplasmablast population in the process of human B cell to plasma cell differentiation. J Immunol. Oct. 15, 2011;187(8):3931-41. doi: 10.4049/jimmunol.1101230. Epub Sep. 14, 2011.

Juilland et al., CARMA1- and MyD88-dependent activation of Jun/ATF-type AP-1 complexes is a hallmark of ABC diffuse large B-cell lymphomas. Blood. Apr. 7, 2016;127(14):1780-9. doi:10.1182/blood-2015-07-655647. Epub Jan. 8, 2016.

Kawagoe et al., Sequential control of Toll-like receptor-dependent responses by IRAKI and IRAK2. Nat Immunol. Jun. 2008;9(6):684-91.

Kiss et al., Comparative testing of peripheral blood and bone marrow for BCR-ABL transcripts in patients post allogeneic bone marrow transplantation and during interferon treatment for chronic myeloid leukemia. Leuk Lymphoma. Aug. 1999;34(5-6):493-500.

Kriangkum et al., Clonotypic IgM V/D/J sequence analysis in Waldenstrom macroglobulinemia suggests an unusual B-cell origin and an expansion of polyclonal B cells in peripheral blood. Blood. Oct. 1, 2004;104(7):2134-42. Epub Feb. 5, 2004.

Kyle et al., IgM monoclonal gammopathy of undetermined significance and smoldering Waldenström's macroglobulinemia. Clin Lymphoma Myeloma. Mar. 2009;9(1):17-8.

Kyle et al., Prognostic markers and criteria to initiate therapy in Waldenstrom's macroglobulinemia: consensus panel recommendations from the Second International Workshop on Waldenstrom's Macroglobulinemia. Semin Oncol. Apr. 2003;30(2):116-20.

Kyrtsonis et al., CD138 expression helps distinguishing Waldenström's macroglobulinemia (WM) from splenic marginal zone lymphoma (SMZL). Clin Lymphoma Myeloma Leuk. Feb. 2011;11(1):99-102. doi: 10.3816/CLML.2011.n.019.

Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.

Lam et al., Cooperative signaling through the signal transducer and activator of transcription 3 and nuclear factor-{kappa}B pathways in subtypes of diffuse large B-cell lymphoma. Blood. Apr. 1, 2008;111(7):3701-13. Epub Dec. 26, 2007.

Landgren et al., MYD88 L265P somatic mutation in IgM MGUS. N Engl J Med. Dec. 6, 2012;367(23):2255-6; author reply 2256-7. doi: 10.1056/NEJMc1211959#SA1.

Lee et al., The mutation spectrum revealed by paired genome sequences from a lung cancer patient. Nature. May 27, 2010;465(7297):473-7.

Leleu et al., Targeting NF-kappaB in Waldenstrom macroglobulinemia. Blood. May 15, 2008;111(10):5068-77.

Leleu et al., The Akt pathway regulates survival and homing in Waldenstrom macroglobulinemia. Blood. Dec. 15, 2007;110(13):4417-26. Epub Aug. 30, 2007.

Lin et al., Helical assembly in the MyD88-IRAK4-IRAK2 complex in TLR/IL-1R signaling. Nature. Jun. 17, 2010;465(7300):885-90.

Lin et al., Lymphoid neoplasms associated with IgM paraprotein: a study of 382 patients. Am J Clin Pathol. Feb. 2005;123(2):200-5.

Loiarro et al., Identification of critical residues of the MyD88 death domain involved in the recruitment of downstream kinases. J Biol Chem. Oct. 9, 2009;284(41):28093-103.

Loiarro et al., Peptide-mediated interference of TIR domain dimerization in MyD88 inhibits interleukin-1-dependent activation of NF-{kappa}B. J Biol Chem. Apr. 22, 2005;280(16):15809-14. Epub Mar. 8, 2005.

Loiarro et al., Pivotal Advance: Inhibition of MyD88 dimerization and recruitment of IRAKI and IRAK4 by a novel peptidomimetic compound. J Leukoc Biol. Oct. 2007;82(4):801-10. Epub Jun. 4, 2007.

Martínez et al., Whole-exome sequencing in splenic marginal zone lymphoma reveals mutations in genes involved in marginal zone differentiation. Leukemia. Jun. 2014;28(6):1334-40. doi: 10.1038/leu.2013.365. Epub Dec. 3, 2013.

McDermott et al., A phase 1 clinical trial of long-term, low-dose treatment of WHIM syndrome with the CXCR4 antagonist plerixafor. Blood. Apr. 10, 2014;123(15):2308-16. doi:10.1182/blood-2013-09-527226. Epub Feb. 12, 2014.

McDermott et al., AMD3100 is a potent antagonist at CXCR4(R334X), a hyperfunctional mutant chemokine receptor and cause of WHIM syndrome. J Cell Mol Med. Oct. 2011;15(10):2071-81. doi: 10.1111/j.1582-4934.2010.01210.x.

McDermott et al., The CXCR4 antagonist plerixafor corrects panleukopenia in patients with WHIM syndrome. Blood. Nov. 3, 2011;118(18):4957-62. doi: 10.1182/blood-2011-07-368084. Epub Sep. 2, 2011.

McMaster et al., Long-term evaluation of three multiple-case Waldenstrom macroglobulinemia families. Clin Cancer Res. Sep. 1, 2007;13(17):5063-9.

Messeguer et al., PROMO: detection of known transcription regulatory elements using species-tailored searches. Bioinformatics. Feb. 2002;18(2):333-4.

Mueller et al., Hierarchical organization of multi-site phosphorylation at the CXCR4 C terminus. PLoS One. May 29, 2013;8(5):e64975. doi: 10.1371/journal.pone.0064975. Print 2013.

Musumeci et al., Hck inhibitors as potential therapeutic agents in cancer and HIV infection. Curr Med Chem. 2015;22(13):1540-64.

(56) References Cited

OTHER PUBLICATIONS

Ngo et al., Oncogenically active MYD88 mutations in human lymphoma. Nature. Feb. 3, 2011;470(7332):115-9. doi: 10.1038/nature09671.
Ngo et al., SDF-1/CXCR4 and VLA-4 interaction regulates homing in Waldenstrom macroglobulinemia. Blood. Jul. 1, 2008;112(1):150-8. doi: 10.1182/blood-2007-12-129395. Epub Apr. 30, 2008.
O'Boyle et al., Open Babel: An open chemical toolbox. J Cheminform. Oct. 7, 2011;3:33. doi:10.1186/1758-2946-3-33.
Okada et al., Autopsy case of lymphoplasmacytic lymphoma with a large submucosal tumor in the stomach. Pathol Int. Oct. 2001;51(10):802-6.
Okuzumi et al., Inhibitor hijacking of Akt activation. Nat Chem Biol. Jul. 2009;5(7):484-93. doi:10.1038/nchembio.183. Epub May 24, 2009.
Ondrejka et al., MYD88 L265P somatic mutation: its usefulness in the differential diagnosis of bone marrow involvement by B-cell lymphoproliferative disorders. Am J Clin Pathol. Sep. 2013;140(3):387-94. doi: 10.1309/AJCP10ZCLFZGYZIP.
Owen et al., Clinicopathological definition of Waldenstrom's macroglobulinemia: consensus panel recommendations from the Second International Workshop on Waldenstrom's Macroglobulinemia. Semin Oncol. Apr. 2003;30(2):110-5.
Passamonti, How I treat polycythemia vera. Blood. Jul. 12, 2012;120(2):275-84. doi: 10.1182/blood-2012-02-366054. Epub May 18, 2012.
Patricelli et al., In situ kinase profiling reveals functionally relevant properties of native kinases. Chem Biol. Jun. 24, 2011;18(6):699-710. doi:10.1016/j.chembiol.2011.04.011.
Pecquet et al., The Src tyrosine kinase Hck is required for Tel-Abl-but not for Tel-Jak2-induced cell transformation. Oncogene. Mar. 8, 2007;26(11):1577-85. Epub Sep. 4, 2006.
Pene-Dumitrescu et al., An inhibitor-resistant mutant of Hck protects CML cells against the antiproliferative and apoptotic effects of the broad-spectrum Src family kinase inhibitor A-419259. Oncogene. Nov. 27, 2008;27(56):7055-69. doi:10.1038/onc.2008.330. Epub Sep. 15, 2008.
Poh et al., Hematopoietic cell kinase (HCK) as a therapeutic target in immune and cancer cells. Oncotarget. Jun. 30, 2015;6(18):15752-71.
Poulain et al., MYD88 L265P mutation in Waldenstrom macroglobulinemia. Blood. May 30, 2013;121(22):4504-11. doi: 10.1182/blood-2012-06-436329. Epub Mar. 26, 2013.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Puente et al., Whole-genome sequencing identifies recurrent mutations in chronic lymphocytic leukaemia. Nature. Jun. 5, 2011;475(7354):101-5. doi:10.1038/nature10113.
Roach et al., Analysis of genetic inheritance in a family quartet by whole-genome sequencing. Science. Apr. 30, 2010;328(5978):636-9.
Roccaro et al., A Novel Activating Mutation Of CXCR4 Plays a Crucial Role In Waldenstrom Macroglobulinemia Biology. Blood. 2013;122: Abstract 272.
Roccaro et al., C1013G/CXCR4 acts as a driver mutation of tumor progression and modulator of drug resistance in lymphoplasmacytic lymphoma. Blood. Jun. 26, 2014;123(26):4120-31. doi:10.1182/blood-2014-03-564583. Epub Apr. 7, 2014.
Sahota et al., CD27 in defining memory B-cell origins in Waldenström's macroglobulinemia. Clin Lymphoma Myeloma. Mar. 2009;9(1):33-5. doi: 10.3816/CLM.2009.n.007.
Saito et al., A pyrrolo-pyrimidine derivative targets human primary AML stem cells in vivo. Sci Transl Med. Apr. 17, 2013;5(181):181ra52. doi: 10.1126/scitranslmed.3004387.
Sanner et al., Reduced surface: an efficient way to compute molecular surfaces. Biopolymers. Mar. 1996;38(3):305-20.
Schaeeeer et al., Signaling through a novel domain of gp130 mediates cell proliferation and activation of Hck and Erk kinases. Mol Cell Biol. Dec. 2001;21(23):8068-81.

Smith et al., In Waldenstrom's macroglobulinemia the quantity of detectable circulating monoclonal B lymphocytes correlates with clinical course. Blood. May 1983;61(5):911-4.
Song et al., The kinase activities of interleukin-1 receptor associated kinase (IRAK)-1 and 4 are redundant in the control of inflammatory cytokine expression in human cells. Mol Immunol. Apr. 2009;46(7):1458-66.
Suh et al., Inhibition of granulocyte-macrophage colony-stimulating factor signaling and microglial proliferation by anti-CD45RO: role of Hck tyrosine kinase and phosphatidylinositol 3-kinase/Akt. J Immunol. Mar. 1, 2005;174(5):2712-9.
Taguchi et al., Characteristic expression of Hck in human B-cell precursors. Exp Hematol. Jan. 2000;28(1):55-64. Erratum in: Exp Hematol. Mar. 2000;28(3):347.
Tai et al., Bruton tyrosine kinase inhibition is a novel therapeutic strategy targeting tumor in the bone marrow microenvironment in multiple myeloma. Blood. Aug. 30, 2012;120(9):1877-87. doi: 10.1182/blood-2011-12-396853. Epub Jun. 11, 2012.
Tai et al., Targeting Brouton's Tyrosine Kinase with PCI-32765 Blocks Growth and Survival of Multiple Myeloma and Waldenström Macroglobulinemia via Potent Inhibition of Osteoclastogenesis, Cytokines/Chemokine Secretion, and Myeloma Stem-Like Cells in the Bone Marrow Microenvironment. Blood. Nov. 18, 2011;118(21):404.
Tiacci et al., Simple genetic diagnosis of hairy cell leukemia by sensitive detection of the BRAF-V600E mutation. Blood. Jan. 5, 2012;119(1):192-5. doi:10.1182/blood-2011-08-371179. Epub Oct. 25, 2011. Erratum in: Blood. Aug. 29, 2013;122(9):1685.
Treon et al., A new era for Waldenstrom macroglobulinemia: MYD88 L265P. Blood. May 30, 2013;121(22):4434-6. doi: 10.1182/blood-2013-04-494849.
Treon et al., A Prospective Multicenter Study Of The Bruton's Tyrosine Kinase Inhibitor Ibrutinib In Patients With Relapsed Or Refractory Waldenstrom's Macroglobulinemia. Blood. 2013;122:Abstract 251.
Treon et al., A prospective, multicenter, phase II study of the Bruton's Tyrosine Kinase Inhibitor Ibrutinib in patients with relapsed and refractory Waldenstrom's Macroglobulinemia. Hematol Oncol. Jun. 2013;31(S1): Abstract 067.
Treon et al., Characterization of familial Waldenstrom's macroglobulinemia. Ann Oncol. Mar. 2006;17(3):488-94. Epub Dec. 15, 2005.
Treon et al., Ibrutinib in previously treated Waldenström's macroglobulinemia. N Engl J Med. Apr. 9, 2015;372(15): 1430-40. doi:10.1056/NEJMoa1501548.
Treon et al., Multicenter clinical trial of bortezomib in relapsed/refractory Waldenstrom's macroglobulinemia: results of WMCTG Trial 03-248. Clin Cancer Res. Jun. 1, 2007;13(11):3320-5.
Treon et al., MYD88 L265P somatic mutation in Waldenström's macroglobulinemia. N Engl J Med. Aug. 30, 2012;367(9):826-33. doi:10.1056/NEJMoa1200710.
Treon et al., MYD88 Mutations and Response to Ibrutinib in Waldenström's Macroglobulinemia. N Engl J Med. Aug. 6, 2015;373(6):584-6. doi:10.1056/NEJMc1506192.
Treon et al., Prospective phase II clinical trial of carfilzomib, rituximab, and dexamethasone (CaRD) in Waldenstrom's macroglobulinemia. 12th International Conference on Malignant Lymphoma. Palazzo dei Congressi, Lugano, Switzerland, Jun. 19-22, 2013, abstract 150, 2013.
Treon et al., Prospective, Multicenter Study of the MTOR Inhibitor Everolimus (RAD001) As Primary Therapy in Waldenstrom's Macroglobulinemia. Blood. 2011;118:Abstract 2951.
Treon et al., Somatic mutations in MYD88 and CXCR4 are determinants of clinical presentation and overall survival in Waldenstrom macroglobulinemia. Blood. May 1, 2014;123(18):2791-6. doi:10.1182/blood-2014-01-550905. Epub Feb. 19, 2014.
Treon et al., Whole Genome sequencing reveals a widely expressed mutation (MYD88 L265P) in Waldenstrom's Macroglobulinemia. Oral and Poster Abstracts. Dec. 2011. 1 Page.
Treon, How I treat Waldenstrom macroglobulinemia. Blood. Sep. 17, 2009;114(12):2375-85.
Trøen et al., CD79B and MYD88 Mutations in Splenic Marginal Zone Lymphoma. ISRN Oncol. 2013;2013:252318. doi: 10.1155/2013/252318. Epub Jan. 10, 2013.

(56) References Cited

OTHER PUBLICATIONS

Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334.

Varettoni et al., Prevalence and clinical significance of the MYD88 (L265P) somatic mutation in Waldenstrom's macroglobulinemia and related lymphoid neoplasms. Blood. Mar. 28, 2013;121(13):2522-8. doi: 10.1182/blood-2012-09-457101. Epub Jan. 25, 2013.

Wang et al., CD19: a biomarker for B cell development, lymphoma diagnosis and therapy. Experimental Hematol Oncol. 2012;1(36):1-7.

Wang et al., IRAK-4 inhibitors for inflammation. Curr Top Med Chem. 2009;9(8):724-37.

Watters et al., Structure, function and regulation of the Toll/IL-1 receptor adaptor proteins. Immunol Cell Biol. Aug.-Sep. 2007;85(6):411-9. Epub Jul. 31, 2007.

Willenbacher et al., Improved accuracy of discrimination between IgM multiple myeloma and Waldenström macroglobulinaemia by testing for MYD88 L265P mutations. Br J Haematol. Jun. 2013;161(6):902-4. doi:10.1111/bjh.12313. Epub Apr. 5, 2013.

Wilson et al., Targeting B cell receptor signaling with ibrutinib in diffuse large B cell lymphoma. Nat Med. Aug. 2015;21(8):922-6. doi: 10.1038/nm.3884. Epub Jul. 20, 2015.

Woyach et al., Resistance mechanisms for the Bruton's tyrosine kinase inhibitor ibrutinib. N Engl J Med. Jun. 12, 2014;370(24):2286-94. doi: 10.1056/NEJMoa1400029. Epub May 28, 2014.

Xu et al., Detection Of MYD88 L265P In Peripheral Blood Of Patients With Waldenström's Macroglobulinemia and IgM Monoclonal Gammopathy Of Undetermined Significance. Blood. 2013;122(21): Abstract 3024.

Xu et al., Detection of MYD88 L265P in peripheral blood of patients with Waldenström's Macroglobulinemia and IgM monoclonal gammopathy of undetermined significance. Leukemia. Aug. 2014;28(8):1698-704. doi: 10.1038/leu.2014.65. Epub Feb. 10, 2014.

Xu et al., Detection of the MYD88 L265P mutation in Waldenström's macroglobulinemia using a highly sensitive allele-specific PCR assay. J Clinical Oncology. May 2012;30(15):8042. Abstract.

Xu et al., MYD88 L265P in Waldenström macroglobulinemia, immunoglobulin M monoclonal gammopathy, and other B-cell lymphoproliferative disorders using conventional and quantitative allele-specific polymerase chain reaction. Blood. Mar. 14, 2013;121(11):2051-8. doi: 10.1182/blood-2012-09-454355. Epub Jan. 15, 2013. Erratum in: Blood. Jun. 27, 2013;121(26):5259.

Yang et al., A mutation in MYD88 (L265P) supports the survival of lymphoplasmacytic cells by activation of Bruton tyrosine kinase in Waldenström macroglobulinemia. Blood. Aug. 1, 20135; 122(7):1222-32. doi:10.1182/blood-2012-12-475111. Epub Jul. 8, 2013.

Yang et al., HCK Is a Highly Relevant Target of Ibrutinib in MYD88 Mutated Waldenstrom's Macroglobulinemia and Diffuse Large B-Cell Lymphoma. Blood. 2015;126:705.

Yang et al., HCK is a survival determinant transactivated by mutated MYD88, and a direct target of ibrutinib. Blood. Jun. 23, 2016;127(25):3237-52. doi:10.1182/blood-2016-01-695098. Epub May 3, 2016.

Yang et al., Tyrosine kinase inhibition in diffuse large B-cell lymphoma: molecular basis for antitumor activity and drug resistance of dasatinib. Leukemia. Sep. 2008;22(9):1755-66. doi:10.1038/leu.2008.163. Epub Jul. 3, 2008.

Ye et al., t(1;14) and t(11 ;18) in the differential diagnosis of Waldenström's macroglobulinemia. Mod Pathol. Sep. 2004;17(9):1150-4.

Young et al., Survival of human lymphoma cells requires B-cell receptor engagement by self-antigens. Proc Natl Acad Sci U S A. Nov. 3, 2015;112(44):13447-54. doi: 10.1073/pnas.1514944112. Epub Oct. 19, 2015.

U.S. Appl. No. 14/128,241, filed Mar. 18, 2014, Allowed.
U.S. Appl. No. 15/021,323, filed Mar. 11, 2016, Allowed.
U.S. Appl. No. 15/102,304, filed Jun. 6, 2016, Published.
U.S. Appl. No. 15/581,736, filed Nov. 23, 2017, Allowed.
EP12807230.3, Feb. 2, 2015, Extended European Search Report.
EP14844516.6, Mar. 28, 2017, Extended European Search Report.
PCT/US2012/044956, Oct. 1, 2012, Invitation To Pay Additional Fees.
PCT/US2012/044956, Dec. 17, 2012, International Search Report and Writtten Opinion.
PCT/US2012/044956, Jan. 16, 2014, International Preliminary Report on Patentability.
PCT/US2014/055386, Dec. 23, 2014, International Search Report and Written Opinion.
PCT/US2014/055386, Mar. 24, 2016, International Preliminary Report on Patentability.
PCT/US2014/068579, Mar. 3, 2015, International Search Report and Written Opinion.
PCT/US2014/068579, Jun. 16, 2016, International Preliminary Report on Patentability.
PCT/US2017/030116, Aug. 21, 2017, International Search Report and Written Opinion.
PCT/US2017/030116, Nov. 8, 2018, International Preliminary Report on Patentability.

Burchat et al., Pyrazolo[3,4-d]pyrimidines containing an extended 3-substituent as potent inhibitors of Lck—a selectivity insight. Bioorg Med Chem Lett. Jun. 17, 2002;12(12):1687-90. doi:10.1016/s0960-894x(02)00196-8. PMID: 12039591.

Ke et al., Anomalous constitutive Src kinase activity promotes B lymphoma survival and growth. Mol Cancer. Dec. 31, 2009;8:132. doi: 10.1186/1476-4598-8-132. PMID: 20043832; PMCID: PMC2814804.

FIG. 1A
FIG. 1B
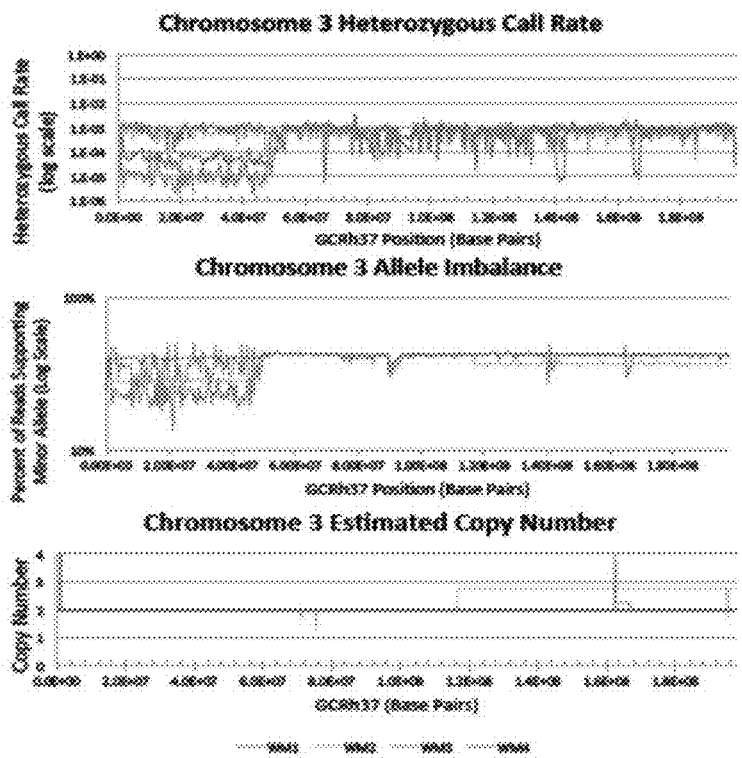
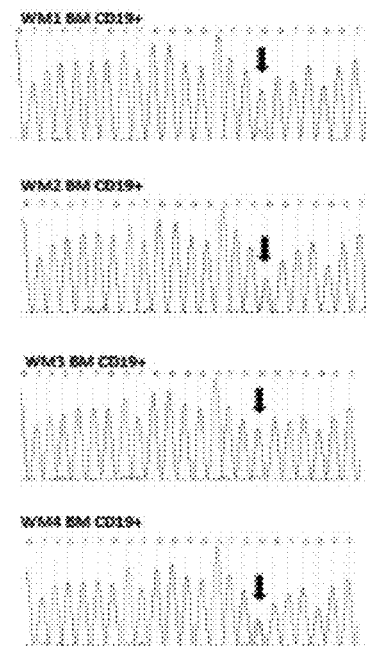
FIG. 1C
FIG. 1D
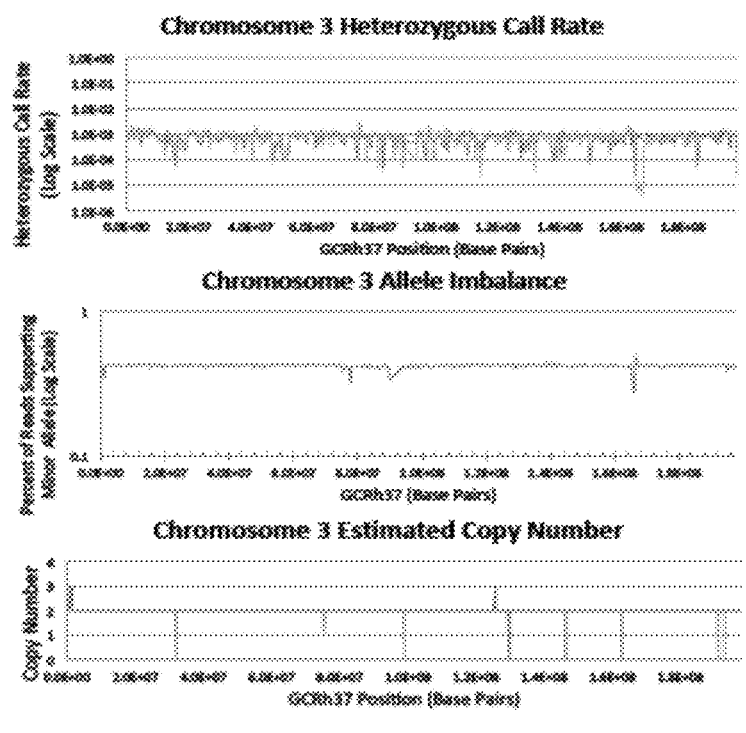
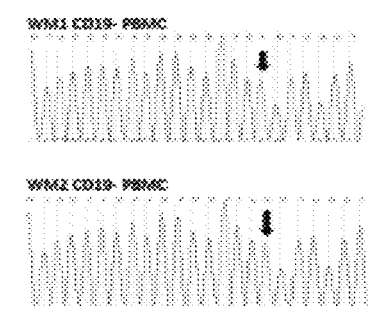

(SEQ ID NO: 9)

1: DMSO; 2: PCI-32765 (1.0μM); 3: MYD88 inhibitory peptides (100μM); 4: PCI-32765 + MYD88 inhibitory peptides.

CI: Combination Index;
CI<1: synergistic effect.

DISCOVERY OF A SOMATIC MUTATION IN MYD88 GENE IN LYMPHOPLASMACYTIC LYMPHOMA

RELATED APPLICATIONS

This application is a continuation of U.S. application Ser. No. 14/128,241, filed Mar. 18, 2014 which is a national stage filing under 35 U.S.C. § 371 of International Application PCT/US2012/044956, filed Jun. 29, 2012, which was published under PCT Article 21(2) in English, and which claims the benefit under 35 U.S.C. § 119(e) of U.S. provisional application Ser. No. 61/571,657, filed Jul. 1, 2011, the disclosure of each referenced application is incorporated by reference herein in its entirety.

BACKGROUND OF THE INVENTION

Waldenstrom's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. Genetic factors play an important role in the pathogenesis of WM, with 25% of patients demonstrating a family history. IgM monoclonal gammopathy of unknown significance (MGUS) often precedes the development of WM. The primary oncogenic event resulting in malignant transformation in WM remains to be delineated. Knowledge of such genomic alteration(s) may permit advances in diagnostic testing, and development of targeted therapies.

SUMMARY OF THE INVENTION

It has been discovered, surprisingly, that a somatic mutation in the myeloid differentiation primary response (MYD88) gene is associated with lymphoplasmacytic lymphoma. Accordingly, in some aspects, the invention involves, facilitating the diagnosis of lymphoplasmacytic lymphoma in a subject by selecting a subject on the basis that the subject presents one or more of the following clinical features: anemia, hyper-viscosity, neuropathy, coagulopathies, splenomegaly, hepatomegaly, adenopathy, and an IgM serum paraprotein, obtaining a biological sample of the subject, and determining from the biological sample whether the subject has a mutation at position 38182641 in chromosome 3p22.2, wherein the presence of the mutation is indicative that the subject has lymphoplasmacytic lymphoma. In some embodiments, the subject presents two or more of the clinical features. In some embodiments, the subject presents three or more of the clinical features. In some embodiments, said determining comprises performing an assay to interrogate position 38182641 in chromosome 3p22.2. In some embodiments, the assay comprises allele specific polymerase chain reaction performed using an allele specific primer, wherein the allele specific primer hybridizes at or near its 3' end to the mutation at position 38182641 in chromosome 3p22.2. In some embodiments, the allele specific primer is SEQ ID NO: 5.

According to one aspect of the invention, a method to distinguish lymphoplasmacytic lymphoma from other B cell neoplasms is provided. The method comprises obtaining a biological sample from a subject that presents symptoms of a B cell lymphoma, which symptom does not exclude a diagnosis of lymphoplasmacytic lymphoma. Symptoms of a B cell lymphoma which do not exclude a diagnosis of LPL include asymptomatic localized or generalized peripheral lymphadenopathy, plasmacytic difference, bone marrow involvement, autoimmune thrombocytopenia, end organ damage (renal insufficiency), anemia, hyper-viscosity, neuropathy, coagulopathies, splenomegaly, hepatomegaly, adenopathy, and an IgM serum paraprotein. In some embodiments, said determining comprises performing an assay to interrogate position 38182641 in chromosome 3p22.2. In some embodiments, the assay comprises allele specific polymerase chain reaction performed using an allele specific primer, wherein the allele specific primer hybridizes at or near its 3' end to the mutation at position 38182641 in chromosome 3p22.2. In some embodiments, the allele specific primer is SEQ ID NO: 5.

In some embodiments, the method comprises obtaining a biological sample from a subject that presents symptoms of both LPL and at least one B cell neoplasm selected from the group consisting of nodal marginal zone lymphomas, extranodal marginal zone lymphoma of mucosa-associated lymphoid tissue (MALT lymphoma), splenic B cell marginal zone lymphoma, monoclonal gammopathy of undetermined significance and plasma cell myeloma, determining from the biological sample whether the subject has a mutation at position 38182641 in chromosome 3p22.2, and providing a report whether the subject has a mutation at position 38182641 in chromosome 3p22.2, wherein the presence of the mutation is indicative that the subject has lymphoplasmacytic lymphoma.

According to one aspect of the invention, a method to treat lymphoplasmacytic lymphoma in a subject is provided. The method comprises selecting a subject on the basis that the subject has a mutation at position 38182641 in chromosome 3p22.2. In some embodiments, the subject also presents one or more symptoms or clinical features of LPL, such as, anemia, hyper-viscosity, neuropathy, coagulopathies, splenomegaly, hepatomegaly, adenopathy, and an IgM serum paraprotein. The subject is administered a myeloid differentiation primary response 88 (MYD88) inhibitor, an interleukin receptor associate kinase 1/4 (IRAK-1/4) inhibitor, and/or a Bruton's tyrosine kinase (BTK) inhibitor in an amount effective to treat lymphoplasmacytic lymphoma. In some embodiments, the MYD88 inhibitor is a peptidomimetic compound ST2825. In some embodiments, the IRAK-1/4 inhibitor is N-(2-Morpholinylethyl)-2-(3-nitrobenzoylamido)-benzimidazole. In some embodiments, the BTK inhibitor is Ibrutinib (PCI-32765).

According to one aspect of the invention, a method for monitoring progression or recurrence of lymphoplasmacytic lymphoma in a subject is provided. The method comprises obtaining multiple biological samples of a subject over a period of time, determining from the multiple biological samples the level of a transcript comprising a mutation at position 38182641 in chromosome 3p22.2, wherein a change in the level of the transcript over the period of time is indicative of the progression or recurrence of LPL in the subject. In some embodiments, the subject is undergoing chemotherapy to treat LPL. In some embodiments, the level of the transcript is measured using quantitative real time polymerase chain reaction. In some embodiments, the quantitative real time polymerase chain reaction is performed using an allele specific primer, wherein the allele specific primer hybridizes at or near its 3' end to the mutation at position 38182641 in chromosome 3p22.2. In some embodiments, the allele specific primer is SEQ ID NO: 5.

According to one aspect of the invention, a method for detecting a mutation at position 38182641 in chromosome 3p22.2 in a subject is provided. The method comprises obtaining a biological sample from the subject in need of such detection, determining from the biological sample whether the subject has a mutation at position 38182641 in chromosome 3p22.2 by allele specific polymerase chain reaction performed using an allele specific primer wherein the allele specific primer hybridizes at or near its 3' end to the mutation at position 38182641 in chromosome 3p22.2.

According to one aspect of the invention, a method for facilitating the diagnosis of lymphoplasmacytic lymphoma in a subject is provided. The method comprises selecting a subject on the basis that the subject presents one or more of the following clinical features: anemia, hyper-viscosity, neuropathy, coagulopathies, splenomegaly, hepatomegaly, adenopathy, and an IgM serum paraprotein, obtaining a biological sample of the subject, determining from the biological sample whether the subject has a mutation at position 38182641 in chromosome 3p22.2, and providing a report summarizing statistically significant results indicating that the subject has lymphoplasmacytic lymphoma if the subject has the mutation.

The biological sample includes, but is not limited to, a sample of bone marrow, lymph node, spleen or blood. In some embodiments, the mutation results in a single nucleotide change from T to C in the myeloid differentiation primary response 88 (MYD88) gene. In some embodiments, the mutation results in an amino acid change from leucine to proline at position 265 in the myeloid differentiation primary response 88 protein.

The subject (individual) is a human. In some embodiments, the subject is suspected of LPL and presents one or more of the clinical features of LPL.

Without intending to be bound by the theory of the invention, it is believed that the presence of the mutation in a subject at position 38182641 in chromosome 3p22.2 is predictive of the risk of development of LPL. The presence of the mutation at position 38182641 in chromosome 3p22.2 in a subject having an elevated (abnormal) level of monoclonal IgM serum paraprotein is predictive of the risk of development of LPL. In some embodiments, a method for predicting the risk of development of LPL is provided. The method comprises selecting a subject on the basis that the subject has an elevated (abnormal) level of monoclonal IgM serum paraprotein, and determining whether the subject has a mutation at position 38182641 in chromosome 3p22.2, wherein the presence of the mutation is indicative that the subject is at an increased risk of developing LPL.

It may even be that the few instances where the mutation was present in a subject who is diagnosed with a B cell neoplasm (other than LPL and subtype ABC of diffuse large B cell lymphoma) was a mistaken diagnosis.

These and other aspects of the inventions, as well as various advantages and utilities will be apparent with reference to the Detailed Description. Each aspect of the invention can encompass various embodiments as will be understood.

BRIEF DESCRIPTION OF THE DRAWINGS

FIGS. 1A-1D show acquired uniparental disomy (aUPD) at chromosome 3p encompassing MYD88 as determined by WGS. Chromosome wide data demonstrating copy number neutral loss of heterozygosity with corresponding allele imbalance for patients WM1 and WM3 indicating presence of an aUPD throughout the tumor clone (FIG. 1A). For patients WM2 and WM4, an aUPD was present in a subpopulation of tumor cells as demonstrated by sustained allele imbalance. Confirmatory Sanger sequencing of the MYD88 mutation mirrors allele imbalances observed by WGS (FIG. 1B). Chromosome wide data (FIG. 1C) and confirmatory Sanger sequencing for MYD88 L265 (FIG. 1D) using CD19-depleted PB mononuclear cells for normal tissue comparisons in patients WM1 and WM2. Arrows (FIGS. 1B, 1D) denote variant allele position.

(FIG. 3C). Scatter plot showed two major clusters of WM patients that were separated by 3.2 cycles. The cluster with delta $C_T$ values ranging from 9.6 to 15.2 cycles was similar to healthy donors (delta $C_T$ values ranging from 10.7 to 16.9 cycles). This cluster was determined as MYD88 L265P negative, whereas another cluster with delta $C_T$ values ranging from −0.2 to 6.4 cycles was determined as MYD88 L265P positive (FIG. 3D).

In FIG. 7B, apoptosis analysis was performed using annexin V and PI staining after PCI-32765 and MYD88 homodimerization inhibitor treatment for 24 hrs. 1: DMSO; 2: PCI-32765 (1.0 µM); 3: MYD88 inhibitory peptides (100 µM); 4: PCI-32765+ MYD88 inhibitory peptides. PCI-32765 shows synergistic tumor cell killing in combination with an IRAK 1/4 kinase inhibitor (FIG. 7C).

DETAILED DESCRIPTION OF THE INVENTION

Figure 2A:
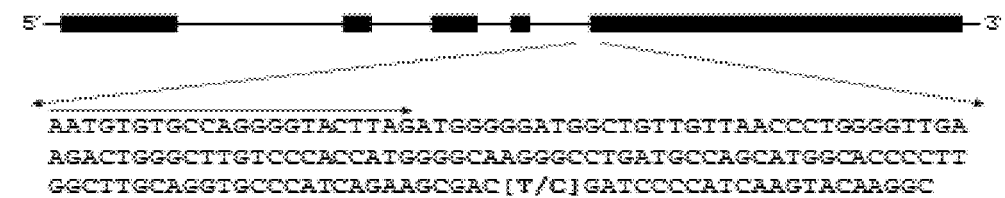
FIGS. 2A-2D show agarose gel-based AS-PCR assay for detection of MYD88 L265P. The reverse primers with an internal mismatch in the third position from the 3'-end and the common forward primer were indicated by the arrows (FIG. 2A). Sanger sequencing confirmed that DLBCL cell line OCI-LY3 carried homozygous MYD88 L265P, whereas OCI-LY19 was wild-type for MYD88 L265P. The position of L265P was indicated by arrow (FIG. 2B). Sensitivity of the AS-PCR assay was assessed by a serial dilution of the MYD88 L265P mutant DNA from OCI-LY3 with the wild-type DNA from OCI-LY19. The PCR products (159-bp) were separated on 2% agarose gel and indicated by arrows (FIG. 2C). The mutant MYD88 L265P allele can consistently be detected at a dilution of 0.1%. An example of WM patients who carried homozygous MYD88 L265P. This patient had 70% BM involvement (FIG. 2D).

The present invention, in one aspect, relates to the surprising discovery of a somatic mutation in the myeloid differentiation primary response (MYD88) gene in patients with lymphoplasmacytic lymphoma. In particular, the invention is based on the identification of a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P). While previous work has identified the same mutation in subtype ABC of diffuse large B cell lymphoma, this previous work did not make any association between the mutation and lymphoplasmacytic lymphoma.

Since the molecular mechanism of LPL was unknown, the differential diagnosis of many diseases that are morphologically similar to LPL was hampered. The discovery set forth in the instant application helps to discriminate LPL from other overlapping entities, and allows for disease specific treatment targeting.

According to one aspect, the present invention provides diagnostic assays for facilitating or aiding in the diagnosis of lymphoplasmacytic lymphoma (LPL) in a subject. LPL is a neoplasm of small B lymphocytes, plasma cytoid lymphocytes, and plasma cells, usually involving bone marrow (BM) and sometime lymph nodes and spleen. Waldenstrom macroglobulinemia (WM) is found in a significant subset of patients with LPL and is defined as LPL with BM involvement and an IgM monoclonal gammopathy of any concentration.

According to one aspect of the invention, a subject is selected for assessment of a mutation at position 38182641 in chromosome 3p22.2 on the basis that the subject is suspected of having LPL, and a biological sample of the subject is assessed for the presence of a mutation. The presence of the mutation is indicative that the subject has LPL. As used herein, "selecting a subject" means identifying a subject that presents one or more clinical features of LPL for further diagnostic analysis. The one or more clinical features of LPL include anemia, hyper-viscosity, neuropathy, coagulopathies, splenomegaly, hepatomegaly, adenopathy, and an IgM serum paraprotein. In some embodiments, a subject presenting two or more, three or more, four or more, five or more, six or more, or seven or more of these clinical features is selected. The subject is selected by a medical practitioner (e.g., a doctor, nurse, clinical laboratory practitioner, genetic counselor, etc.), a healthcare organization, or a clinical laboratory.

Non-limiting examples of the biological sample include bone marrow, lymph node, spleen or blood. Obtaining a biological sample of a subject means taking possession of a biological sample of the subject. Obtaining a biological sample from a subject means removing a biological sample from the subject. Therefore, the person obtaining a biological sample of a subject and determining the presence of the mutation in the sample does not necessarily obtain the biological sample from the subject. In some embodiments, the biological sample may be removed from the subject by a medical practitioner (e.g., a doctor, nurse, or a clinical laboratory practitioner), and then provided to the person determining the presence of the mutation. The biological sample may be provided to the person determining the mutation by the subject or by a medical practitioner (e.g., a doctor, nurse, or a clinical laboratory practitioner). In some embodiments, the person determining the mutation obtains a biological sample from the subject by removing the sample from the subject.

The term "mutation" means any change or difference in the nucleic acid or protein sequence of MYD88 as compared to the wild type sequence that results in the activation of MYD88 which leads to the activation of NF-κB. Mutations include, but are not limited to, nonsense mutations, missense mutations, frameshift mutations, rearrangement mutations, insertion mutations and deletion mutations. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P).

One skilled in the art will appreciate that many suitable methods, in addition to and including the ones discussed in the examples, can be used to detect mutations in the MYD88 gene. Detection methods that can be used include, but are not limited to, direct sequencing, DNAchip technologies, mass spectroscopy, polymerase chain reaction (PCR), allele specific polymerase chain reaction, real time polymerase chain reaction, reverse transcriptase PCR, electrophoretic mobility, nucleic acid hybridization, fluorescent in situ hybridization, and denaturing high performance liquid chromatography.

In some embodiments, mutations in the MYD88 gene may be detected by allele specific polymerase chain reaction (AS-PCR). For AS-PCR, allele specific primers are used which hybridize at or near their 3' ends to a particular mutation in the MYD88 gene. If the mutation is not present, the 3'-terminal mismatched primer does not initiate replication, and an amplification product is not observed. In some embodiments, only the forward primer or the reverse primer hybridizes at or near its 3' ends to a particular mutation in the MYD88 gene. In some embodiments, both the forward and the reverse primer hybridize at or near their 3' ends to a particular mutation in the MYD88 gene. In some embodiments, the allele specific primer is SEQ ID NO: 5. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P).

In some embodiments, mutations in the MYD88 gene may be detected by the direct sequencing of nucleic acid molecules. Techniques for the direct sequencing of DNA are well known in the art. In one embodiment of the invention, mutations may be detected by Sanger sequencing, which may include the use of a thermostable polymerase enzyme, a sequencing primer, dNTPs and limiting amounts of chain terminating fluorescently or radioactively labeled ddNTPs. Polyacrylamide gel electrophoresis or another technique such as capillary electrophoresis may be used to separate the products of the sequencing reactions followed by the detection of the fluorescent or radioactive labels. In one example of this embodiment of the invention, mutations in MYD88 could be determined using automated sequencing on an Applied Biosystems 3700 DNA Analyzer or 3730×1 DNA Analyzer™. Mutations may be identified by comparing the sequence of a subject to that of a wildtype individual or to reference sequences found in the public databases.

Other embodiments of the invention contemplate the use of DNA chip technologies for the detection of mutations within the MYD88 gene. Among other applications, DNA chip technologies allow for the identification of mutations within the sequences of the intention through the analysis of the hybridization patterns of a nucleic acid sample onto a high-density spatially addressable microarray of predetermined sequences.

Another technique for the detection of mutations is denaturing HPLC analysis. Accordingly, one embodiment of the invention includes the use of a Transgenomic Wave™ machine for the dHPLC analysis of nucleic acids for the identification of heterozygous mutations or polymorphisms within the sequences of the invention.

The invention also contemplates the use of mass spectroscopy for the genotyping of mutations. Mutant and wildtype nucleic acid molecules may differ in mass due to the different composition of wildtype and mutant sequences, allowing for the identification of mutations on the basis of the molecular mass of different nucleotide sequences. The use of mass spectroscopy, and in particular Matrix Assisted Laser Desorption Ionisation Time of Flight (MALDI-TOF) mass spectroscopy for the genotyping of mutations is well known by those skilled in the relevant art. For example, U.S. Pat. No. 6,043,031 describes a fast and highly accurate mass spectrometer based process for detecting a particular nucleic acid sequence. The MassARRAY™ platform from SEQUENOM™ is an example of a commercially available system capable of genotyping single nucleotide polymorphisms and detecting the mutations in genes.

According to one aspect, the present invention provides a method to distinguish lymphoplasmacytic lymphoma from other B cell neoplasms selected from the group consisting of nodal marginal zone lymphomas, extranodal marginal zone lymphoma of mucosa-associated lymphoid tissue (MALT lymphoma), splenic B cell marginal zone lymphoma, monoclonal gammopathy of undetermined significance and plasma cell myeloma. The method comprises selecting or identifying a subject that presents one or more symptoms or clinical features of LPL which overlap with one or more symptoms of at least one of the B cell neoplasms described above. Thus, the subject is an individual who is suspected of having either LPL or one of the other B cell neoplasm. The subject is selected for further diagnostic analysis by a medical practitioner (e.g., a doctor, nurse, clinical laboratory practitioner, genetic counselor, etc.), a healthcare organization, or a clinical laboratory.

The one or more symptoms or clinical features of LPL include anemia, hyper-viscosity, neuropathy, coagulopathies, splenomegaly, hepatomegaly, adenopathy, and an IgM serum paraprotein. In addition, the subject may also present one or more of the following clinical features or symptoms of other B cell neoplasms: asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia. The subject suspected of having either LPL or one of the other B cell neoplasm is assessed for the presence of a mutation at position 38182641 in chromosome 3p22.2, wherein the presence of the mutation is indicative that the subject has LPL.

A report summarizing the results of the analysis, i.e. the presence or absence of the mutation and any other information pertaining to the analysis could optionally be generated as part of the analysis (which may be interchangeably referred to herein as "providing" a report, "producing" a report, or "generating" a report). Examples of reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example). In addition to, or as an alternative to, generating a tangible report, reports can also be displayed on a computer screen (or the display of another electronic device or instrument).

A report can further be transmitted, communicated or reported (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party intended to view or possess the report. The act of 'transmitting' or 'communicating' a report can be by any means known in the art, based on the form of the report, and includes both oral and non-oral transmission. Furthermore, "transmitting" or "communicating" a report can include delivering a report ("pushing") and/or retrieving ("pulling") a report. For example, non-oral reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

According to one aspect of the invention, a method to treat LPL is provided. The method comprises selecting a subject on the basis that the subject has a mutation at position 38182641 in chromosome 3p22.2, and administering to the subject a myeloid differentiation primary response 88 (MYD88) inhibitor, an interleukin receptor associate kinase 1/4 (IRAK-1/4) inhibitor, and/or a Bruton's tyrosine kinase (BTK) inhibitor in an amount effective to treat lymphoplasmacytic lymphoma. A non-limiting example of an MYD88 inhibitor includes the peptidomimetic compound ST2825 (WO 2006/06709). A non-limiting example of an IRAK-1/4 inhibitor is N-(2-Morpholinylethyl)-2-(3-nitrobenzoylamido)-benzimidazole. In some embodiments, BTK inhibitors useful in the instant invention block MYD88 L265P and BTK signaling. A non-limiting example of a BTK inhibitor includes Ibrutinib (PCI-32765).

In some embodiments, the method comprises selecting a subject on the basis that the subject has a mutation at position 38182641 in chromosome 3p22.2 and presents one or more symptoms of LPL. The selected subject is treated using an effective amount of bortezomib (Velcade®), bendamestine, alemtuzumab, and/or rituximab, but not bisphosphonates or fludarabine.

The MYD88 inhibitor, IRAK-1/4 inhibitor, and/or BTK inhibitor are administered in an effective amount. An effective amount is a dose sufficient to provide a medically desirable result and can be determined by one of skill in the art using routine methods. In some embodiments, an effective amount is an amount which results in any improvement in the condition being treated. In some embodiments, an effective amount may depend on the type and extent of LPL being treated and/or use of one or more additional therapeutic agents. However, one of skill in the art can determine appropriate doses and ranges of therapeutic agents to use, for example based on in vitro and/or in vivo testing and/or other knowledge of compound dosages.

When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of LPL, an effective amount is that amount which slows the progression of the disease, halts the progression of the disease, or reverses the progression of the disease. An effective amount includes, but is not limited to, that amount necessary to slow, reduce, inhibit, ameliorate or reverse one or more symptoms associated with LPL. In some embodiments, such terms refer to a reduction in the levels of IgM serum paraprotein, anemia, hyper-viscosity, neuropathy, coagulopathies, splenomegaly, hepatomegaly, and adenopathy.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

Pharmaceutical preparations and compounds comprising MYD88 inhibitor, IRAK-1/4 inhibitor, and/or BTK inhibitor are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present invention may include or be diluted into a pharmaceutically-acceptable carrier. The term "pharmaceutically-acceptable carrier" as used herein means one or more compatible fillers, diluants or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

According to one aspect of the invention, a method for monitoring progression or recurrence of lymphoplasmacytic lymphoma in a subject is provided. The method comprises obtaining multiple biological samples of a subject over a period of time, determining from the multiple biological samples the level of a transcript comprising a mutation at position 38182641 in chromosome 3p22.2, wherein an increase in the level of the transcript over the period of time is indicative of the progression or recurrence of LPL in the subject.

As used herein, a transcript comprising a mutation means MYD88 nucleic acid or protein that has a mutation at position 38182641 in chromosome 3p22.2. The level of the transcript comprising a mutation at position 38182641 in chromosome 3p22.2 can be determined by any means known to one skilled in the art, including, but not limited to Western blot, Northern blot, and quantitative real time polymerase chain reaction. In some embodiments, quantitation of the transcript levels is accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art. In some embodiments, the quantitative real time polymerase chain reaction is performed using an allele specific primer, wherein the allele specific primer hybridizes at or near its 3' end to a mutation at position 38182641 in chromosome 3p22.2. In some embodiments, the allele specific primer is SEQ ID NO: 5.

The level of the transcript comprising the mutation is indicative of the state of the disease. In normal (healthy) subjects the mutation is absent. In diseased subjects, the transcript comprising the mutation is expressed at a level consistent with the status (progression) of the disease. Although it is believed that most of the transcription of the MYD88 gene occurs in the bone marrow, levels of the transcript and protein will be present in the circulation because of the normal turnover and presence of dead cells in the blood.

As used herein, a change in the level of the transcript comprising a mutation means that the amount or concentration of the transcript sufficiently changes over time. A change in the level of the transcript over the period of time may be any statistically significant change which is detectable. Such a change may include, but is not limited to, about a 1%, about a 10%, about a 20%, about a 40%, about a 80%, about a 2-fold, about a 4-fold, about an 8-fold, about a 20-fold, or about a 100-fold change over the time. An increase in the level of the transcript indicative of unfavorable progression of the disease, while a decrease in the level of the transcript is indicative of a favorable progression of the disease.

As used herein, a "period of time" is intended to include a period of days, weeks, months or even years. Multiple biological samples of the subject are obtained over a period of time, i.e. a biological sample is obtained periodically over time at various intervals. A biological sample can be obtained at any interval. For example, a biological sample can be taken every day for weeks, months or years. Alternatively, a biological sample can be obtained once a week, or six times a week for a period of weeks, months or years. In one embodiment, a biological sample is obtained once a week over a period of three months. In one embodiment, a biological sample is obtained once a month for a period of months, or years.

In some embodiments, the subject is undergoing chemotherapy to treat LPL. An increase in the level of the transcript over the period of time in a subject undergoing chemotherapy to treat LPL would indicate that there is progression of the disease and that the subject is not responding to the therapy. A decrease in the level of the transcript over the period of time in a subject undergoing chemotherapy to treat LPL would indicate that the subject is responding to the therapy.

According to one aspect of the invention, a method for detecting a mutation at position 38182641 in chromosome 3p22.2 in a subject is provided. The method comprises obtaining a biological sample from the subject in need of such detection, and determining from the biological sample whether the subject has a mutation at position 38182641 in chromosome 3p22.2 by allele specific polymerase chain reaction (AS-PCR). The AS-PCR is performed using an allele specific primer wherein the allele specific primer hybridizes at or near its 3' end to the mutation at position 38182641 in chromosome 3p22.2. In some embodiments, the allele specific primer is SEQ ID NO: 5. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P).

A subject in need of detection may be a subject suspected of having LPL. The subject may present one or more clinical features of LPL including, but not limited to anemia, hyperviscosity, neuropathy, coagulopathies, splenomegaly, hepatomegaly, adenopathy, and an IgM serum paraprotein. In some embodiments, a subject in need of detection may be a subject suspected of having subtype ABC of diffuse large B cell lymphoma. The subject may present one or more clinical features of subtype ABC of diffuse large B cell lymphoma including, but not limited to enlarged lymph node in the neck, groin or abdomen, fever, weight loss, and drenching night sweats. A subject in need of detection may be a subject suspected of having gastric mucosa-associated lymphoid tissue (MALT) lymphoma. The subject may present one or more clinical features of MALT including, but not limited to chronic inflammation caused by *Helicobacter pylori* infection, stomach pain, dyspepsia, nausea, constipation and anemia.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

Thirty patients meeting consensus criteria for the diagnosis of WM were studied by whole genome sequencing (WGS). Their participation was approved by the Institutional Review Board at Dana-Farber Cancer Institute. The characteristics of these patients are summarized in Table 1. Nine of these patients had a familial history of a B-cell malignancy. Bone marrow (BM) and peripheral blood (PB) mononuclear cells from these individuals were obtained after density-gradient centrifugation. Magnetic bead sorting was used for tumor cell isolation (Miltenyi Biotec, Auburn, Calif.). The purity of isolated B-cells (CD19+) by this technique was over 90%, and the median clonal B-cell population by light chain restriction was 96% (Table 1). The median time from diagnosis of WM to BM collection for the 30 patients was 14.1 (range 0-138.2 months). CD19-depleted PB mononuclear cells were collected as matched normal tissue from 19 of the 30 patients, and paired tumor/normal tissue WGS performed for 10 of these patients. The baseline characteristics for these 10 patients did not differ significantly from unpaired patients.

Following cell isolation, high molecular weight DNA was isolated using the Allprep DNA/RNA mini kit (Qiagen, Valencia, Calif.). For 10 patients, WGS of tumor and matched normal samples was performed, and for 20 additional patients tumor samples alone were completely sequenced. Library construction and WGS of paired-end clones was performed by Complete Genomics Inc. (CGI; Mountain View, Calif.) as previously described. Read sequences were aligned to the reference genome (NCBI Build 37) and reads in potentially variant regions (SNVs, insertions, and deletions) were identified and subjected to local de novo assembly. The assembler then scored both variant and homozygous reference consensus calls in each sample using a Bayesian framework which considered read depth, individual base call quality, and mapping probabilities. A likelihood ratio test for each variant (variant score) expressed in decibels (dB) was generated and reported. High confidence somatic variants were identified using CGAT version 1.3 with a somatic score of 0.1 giving an estimated rate of one false somatic single nucleotide variant per 17.7 Mb of DNA. Copy number was estimated by % GC normalized read depth, and acquired uniparental disomy (aUPD) was identified as copy-neutral loss of heterozygosity. In addition allele imbalance was determined by the percentage of reads mapping to the minor allele at heterozygous SNPs which was averaged over 500 Kb.

To validate WGS results, a set of PCR primers were designed to amplify a 726-bp fragment that covers the MYD88 L265P mutation (forward: 5'-ggg ata tgc tga act aag ttg cca c-3'(SEQ ID NO: 1) and reverse: 5'-gac gtg tct gtg aag ttg gca tct c-3' (SEQ ID NO: 2)). Twenty nanograms of genomic DNA were used for PCR amplification. After initial denaturation at 95° C. for 2 minutes, 40 cycles of PCR amplification were performed, each consisting of a denaturing step of 94° C. for 30 seconds, annealing at 65° C. for 30 seconds, and extension at 68° C. for 1 minute, followed by a final step at 68° C. for 10 minutes. The amplified fragments were isolated by QIAquick gel extraction kit (Qiagen, CA) and sequenced using the forward primer 5'-gct gtt gtt aac cct ggg gtt gaa g-3' (SEQ ID NO: 3), and the reverse primer 5'-gac gtg tct gtg aag ttg gca tct c-3' (SEQ ID NO: 4).

Sanger sequencing was used to validate WGS results in tumor samples from all 30 WM patients, and also in normal paired tissue from 19 patients, including the 10 individuals with paired WGS data. In as well, CD19+ and CD138+ isolated BM cells from an unrelated cohort of 12 other WM patients; CD19+ isolated BM cells from 8 IgM MGUS patients; CD138+ isolated BM cells from 8 multiple myeloma (MM) patients; CD19+ isolated PB mononuclear cells from 12 healthy donors; as well as the BCWM.1, MWCL-1, and WM-WSU WM cell lines; the IgM secreting Ramos cell line, and the MM1.S, RPMI 8226, and U266 MM cell lines were also Sanger sequenced for MYD88. TA cloning and sequencing of at least 100 clones was also performed using the above primers for CD19+ isolated BM cells for 4 patients with IgM MGUS (Genewiz, S. Plainfield, N.J.).

Results

Tumor and normal genomes were both sequenced to an average of 66× (range 60-91×) coverage of mapped individual reads. The average gross mapped yield for these genomes was 186.89 (range 171.56-262.03 Gb). In our initial analysis of the 10 paired genomes, we identified a recurring sequence variant with a variant score of 189 (range 74-345) at position 38182641 in chromosome 3p22.2 which results in a single nucleotide change from T→C in the myeloid differentiation primary response (MYD88) gene, and a predicted non-synonymous change at amino acid position 265 from leucine to proline (L265P). This variant was the most common of a median of 3,419 (range 2,540-4,011) somatic variants identified by WGS in the 10 paired patients using a somatic score of 0.1. By WGS, the MYD88 L265 variant was found as a somatic mutation in tumor cells from all 10 paired patients, as it was not found in their matched normal tissues, and was also seen in tumor cells from 16 of the 20 unpaired WM patients. The presence versus absence of the MYD88 L265 mutation in these patients was not impacted by time from WM diagnosis (14.1 versus 14.8 months, respectively; p=0.40). For 22 of 26 patients, the MYD88 L265P variant was heterozygous, whereas in 4 patients an acquired UPD event (median 49.5 MB, range 48.5-50.0 MB) at 3p22.2 resulted in homozygous presence of the variant in at least a subset of tumor cells (FIGS. 1A, 1B). These UPD events were absent in normal tissue for the 2 of 4 patients who had paired samples (FIGS. 1C, 1D). No distinguishing clinical and laboratory features for patients with homozygous versus heterozygous MYD88 L265 mutation were observed, though patients with homozygous MYD88 L265 had a considerably longer interval from WM diagnosis (56.4 versus 11.1 months; p=0.30), and invariably a larger patient series will be required to determine the significance of this finding.

Sanger sequencing confirmed the presence of the MYD88 L265P variant in all 26 tumor samples revealed by WGS, as well as in one additional patient's tumor sample which had read level evidence of the MYD88 L265P variant but was not called with adequate confidence. In this patient, a subpopulation (approximately 10%) of tumor cells exhibited the MYD88 L265P mutation. By Sanger sequencing, the L265P MYD88 variant was therefore present in tumors of 27 of 30 (90%) WM patients, which included patients with sporadic as well as familial disease in whom the variant was observed at the same frequency. Sanger sequencing also confirmed the absence of the MYD88 L265P mutation in normal tissue from the 10 paired patients who underwent WGS, as well as in 9 other unpaired patients who had the MYD88 L265 mutation by WGS, and for whom normal tissue was available.

In an unrelated cohort of 12 WM patients, we further observed by Sanger sequencing a heterozygous MYD88 L265P variant in 11 (92%) patients. Importantly, the MYD88 L265P variant was present in both CD19+ and CD138+ selected cells in these patients consistent with the known distribution of the malignant WM clone which extends from mature B-cells to plasma cells. By Sanger sequencing, we also detected a heterozygous MYD88 L265P variant in BCWM.1 and MWCL-1 WM cells. In contrast, the MYD88 L265P variant was not found in the IgM secreting cell lines WM-WSU and Ramos, both of which carry t(8; 14), and in none of the myeloma cell lines.

Furthermore, we did not detect the MYD88 L265P variant in CD19+ selected B-cells from 12 healthy individuals, nor in tumor samples from 8 of 8 myeloma patients. By direct Sanger sequencing, the MYD88 L265 mutation was absent in 7 of 8 (87.5%) IgM MGUS patients whose characteristics are described in Table 2. In the sole IgM MGUS patient in whom the MYD88 L265P mutation was detected, increased LPC were noted in his BM aspirate, and a core biopsy showed an isolated nodule but no distinct infiltration by LPL cells required for the consensus diagnosis of WM. His subsequent course has been marked by progressively rising IgM levels, and a falling hematocrit. TA cloning and sequencing of at least 100 clones was also undertaken for 4 IgM MGUS patients whose direct Sanger sequencing did not reveal the MYD88 L265 variant. The MYD88 L265 variant was absent in all clones for these 4 IgM MGUS patients. These findings may potentially signify that acquisition of the MYD88 L265 variant represents a transforming event from IgM MGUS to WM, or that the frequency of the MYD88 L265 variant is too low to be picked up in IgM MGUS patients by either WGS or Sanger sequencing. Another consideration is that IgM MGUS might itself be heterogeneous, with acquisition of the MYD88 L265P leading to WM, while in other cases with wild type MYD88, a different oncogenic trajectory may result.

The discovery of a mutation in MYD88 is of significance given its role as an adaptor molecule in Toll-like receptor (TLR) and interleukin-1 receptor (IL-1R) signaling. All of the TLRs except for TLR3 use MYD88 to facilitate their signaling. Following TLR or IL-1R stimulation, MYD88 is recruited to the activated receptor complex as a homodimer which then complexes with IRAK4, leading to its autophosphorylation. The MYD88/IRAK4 complex then recruits and activates IRAK1 and IRAK2. Tumor necrosis factor receptor associated factor 6 (TRAF-6) is then activated by IRAK1 leading to early NF-κB activation, whereas IRAK2 facilitates late NF-κB activation. The L265P mutation in MYD88 occurs at a residue that is highly conserved in evolution, and contributes to a β-sheet at the hydrophobic core of the domain. Staudt and colleagues recently reported the presence of the MYD88 L265P mutation in a subset of tumors taken from patients with the ABC subtype of diffuse large B-cell lymphoma (DLBCL), and in a few patients with gastric mucosa-associated lymphoid tissue (MALT) lymphomas. In contrast, the MYD88 L265P mutation was absent in tumor samples from patients with the GCB subtype of DLBCL, and Burkitt's lymphoma. The frequency of 90% observed for the MYD88 L265 variant in our studies from 2 independent cohorts of WM patients is far more extensive than that observed in DLBCL (29%) and MALT (6%) lymphomas.

Staudt and colleagues also demonstrated that ectopic expression of MYD88 L265P, but not wild type MYD88, prevented apoptosis of L265P expressing ABC DLBCL cell lines that underwent total MYD88 knock down. Co-immunoprecipitation experiments in these cell lines with the L265P mutation also showed enhanced binding to and phosphorylation of IRAK1, which was absent in cells with wild type MYD88. Additionally, knock down studies of MYD88 or IRAK1, or inhibition of IRAK1 function with an IRAK1/4 kinase inhibitor led to loss of NF-κB signaling. Similarly, we have observed that knockdown of MYD88 by lentiviral transduction, and/or treatment with a MYD88 homodimerization inhibitory peptide17 or IRAK1/4 inhibitor18 of BCWM.1 and MWCL-1 WM cells which possess the MYD88 L265P mutation leads to loss of NF-κB signaling and enhanced apoptosis. Since NF-κB signaling represents a critical determinant of WM cell growth and survival, targeting of tonic MYD88/IRAK signaling is of potential relevance to WM therapy.

In summary, using WGS, a novel, widely expressed somatic variant (MYD88 L265P) has been identified in malignant LPC of WM patients, which helps to discriminate WM from other overlapping entities, and whose putative role in NF-κB signaling is of relevance to WM lymphomagenesis. These studies offer novel insights into the pathogenesis of WM, and provide a framework for the development of diagnostic tools and targeted therapies for patients with WM.

Example 2

Materials and Methods
Patient and Samples

Ninety seven patients meeting diagnostic criteria for WM and 40 healthy donors (10 BM and 30 PBMC) were included in this study. Their participation was approved by the IRB at the Dana-Farber Cancer Institute. Bone marrow mononuclear cells (BMMC) were sorted using magnetic beads. Purity of isolated B-cells (CD19+) was over 90%. DNA was extracted using Allprep DNA/RNA mini kit (Qiagen, Valencia, Calif.). DLBCL cell lines OCI-LY3 and OCI-LY19 were kindly provided by Dr. Mark Minden from University Health Network in Canada.

Allele-Specific Polymerase Chain Reaction (AS-PCR)

Two reverse primers were designed to differentiate the mutant and wild-type allele of MYD88 L265P. To optimize the specificity, an internal mismatch in the third position from the 3'-end was introduced. The mutant-specific reverse primer was 5'-CCT TGT ACT TGA TGG GGA aCG-3' (SEQ ID NO: 5) and the wild-type-specific reverse primer was 5'-GCC TTG TAC TTG ATG GGG AaC A-3' (SEQ ID NO: 6). The common forward primer was 5'-AAT GTG TGC CAG GGG TAC TTA G-3' (SEQ ID NO: 7). PCR reaction was performed in a final volume of 25 ul with 50 nM of each primer and 50 ng DNA using PCR SuperMix High Fidelity (Life technology, CA). Thermal cycling conditions were: 2 min at 94° C., followed by 40 cycles of 94° C. for 30 s, 57° C. for 30 s, and 68° C. for 30 s, with a final extension at 68° C. for 5 min. The amplified PCR products (159-bp) were separated on 2% agarose gel. To confirm the sequence, PCR products were purified by QIA quick gel extraction kit (Qiagen, CA) and sequenced using both forward and reverse PCR primers.

Real-Time AS-PCR

Quantitative detection of the MYD88 L265P mutation was developed using the primers described above and Power SYBR® Green PCR Master Mix according to manufacturer's instruction on the ABI Prism 7500 Sequence Detection System (Applied Biosystems, Foster City, Calif.). Briefly, PCR reaction was performed in a final volume of 25 μl with 25 nM of each primer and 50 ng DNA. Thermal cycling conditions were: 10 min at 950 C, followed by 40 cycles of 95° C. for 15 s and 60° C. for 60 s. Each sample was assayed in triplicate. The standard curve for MYD88 L265P was generated by a serial dilution of the mutant DNA with the wild-type DNA (50%, 10%, 2%, 0.4%, 0.08%, and wild-type). For the corresponding reference PCR, the forward primer is same as the one used for the AS-PCR (5'-AAT GTG TGC CAG GGG TAC TTA G-3'; (SEQ ID NO: 7)) and the reverse primer is located at 53-bp downstream of the AS-PCR primer (5'-TGG TGT AGT CGC AGA CAG TGA-3'; (SEQ ID NO: 8)). Levels of the mutant MYD88 L265P in patient samples were calculated based on the value of delta CT and the standard curve.

Sanger Sequencing

The forward PCR primer 5'-GGG ATA TGC TGA ACT AAG TTG CCA C-3' (SEQ ID NO: 1) and reverse PCR primer 5'-GAC GTG TCT GTG AAG TTG GCA TCT C-3' (SEQ ID NO: 4) were designed to amplify a 726-bp fragment covering the MYD88 L265P site. Amplified PCR products were isolated by QIA quick gel extraction kit (Qiagen, CA) and sequenced using the reverse PCR primer and a sequencing primer 5'-GCT GTT GTT AAC CCT GGG GTT GAA G-3' (SEQ ID NO: 3).

Statistical Analysis

Correlation between the MYD88 L265P status and clinical parameters was evaluated by non-parametric ANOVA. Correlation between the changes of BM involvement and levels of mutant MYD88 L265P was assessed by linear regression. All analyses were performed with R (R Foundation for Statistical Computing, Vienna, Austria).

Results

Conventional AS-PCR Design

Figure 2B:
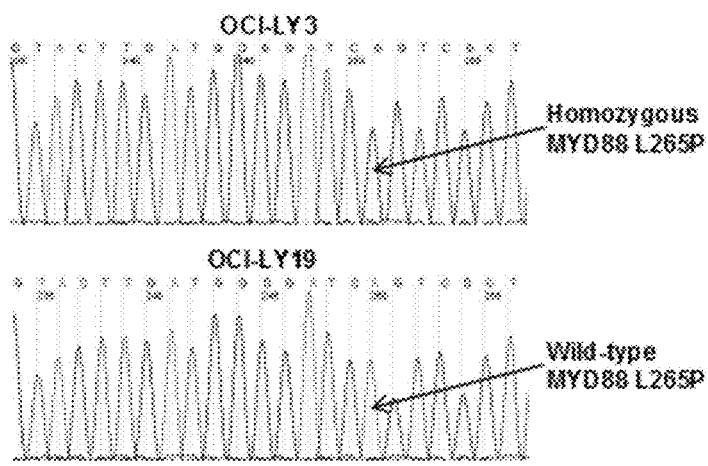
Figure 2C:
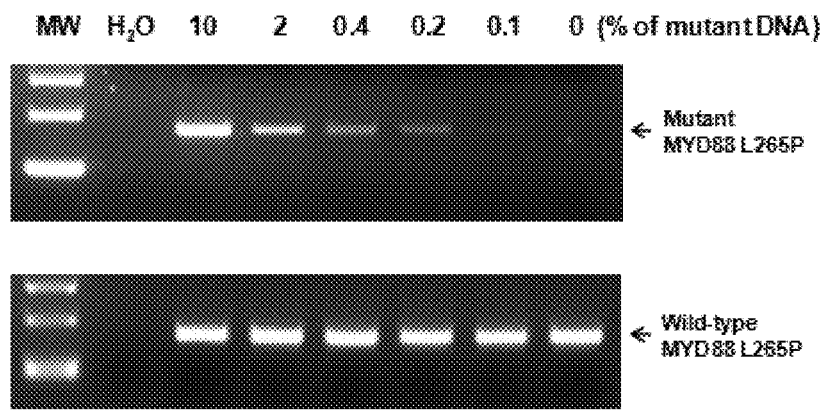

The somatic mutation L265P in the MYD88 gene was found in approximately 90% of WM patients. To efficiently and quickly determine the MYD88 L265P status, an inexpensive AS-PCR assay was developed that can be easily implemented in any laboratories with conventional PCR technology. As shown in FIG. 2A, the AS primers are located in exon 5 while the common forward primer is located in intron 4. To enhance the specificity in the AS-PCR reaction, an additional mismatch (T>A) was introduced at the third position from the 3' end of the AS primers. Sensitivity of the AS-PCR assay was assessed by a serial dilution of the DNA isolated from DLBCL cell line OCI-LY3 (homozygous MYD88 L265P) with the DNA from DLBCL cell line OCI-LY19 (wild-type MYD88 L265P). The MYD88 L265P status of the cell lines was confirmed by Sanger sequencing (FIG. 2B). The sensitivity assessments demonstrated that the mutant allele of MYD88 L265P can consistently be detected at a dilution of 0.1% in the gel-based AS-PCR assay (FIG. 2C).

Figure 2D:
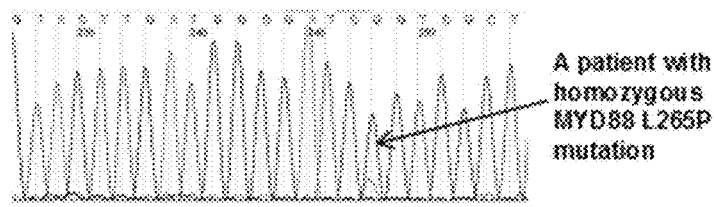

This assay was then applied to 97 WM patients who had not received pharmacological interventions at the time of BM biopsies. 87/97 (89.7%) were found positive for the MYD88 L265P mutation. To further verify the AS-PCR assay, the entire cohort was sequenced for the MYD88 L265P position. Among the 87 patients positive for MYD88 L265P by AS-PCR, 82 were positive while 5 were negative by Sanger sequencing. The 5 patients negative for MYD88 L265P by Sanger sequencing showed weak signals in the gel-based AS-PCR assay. By contrast, all patients negative for MYD88 L265P by AS-PCR remained negative by Sanger sequencing. In addition, DNA from 40 healthy donors (10 BM and 30 PBMC) was analyzed and no MYD88 L265P mutation was detected by either of the methods. The overall results suggest that this AS-PCR assay is simple, reliable, and sensitive. In addition, Sanger sequencing analysis suggested that five patients carried homozygous MYD88 L265P because the mutant allele peak was significantly higher than the wild-type allele peak. FIG. 2D shows an example of the homozygous carriers. This patient had 70% of BM involvement, so that the wild-type allele still can be detected by Sanger sequencing. Homozygous MYD88 L265P could be caused by an acquired uniparental disomy (UPD) event at 3p22.2.

Quantitative Detection of MYD88 L265P Mutation

Figure 3A:
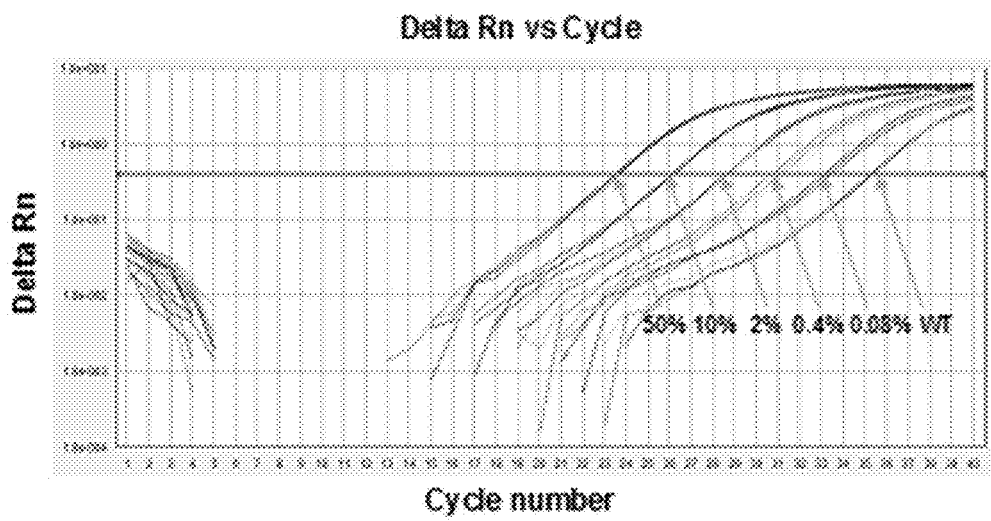
FIGS. 3A-3D show the sensitivity and specificity of the real-time AS-PCR and scatter plot of comparison of MYD88 L265P positive and negative patients and healthy donors. The MYD88 L265P mutant DNA (OCI-LY3) was diluted with the wild-type DNA (OCI-LY19) at the concentration as indicated in the amplification plot. The mutant MYD88 L265P allele can be detected at a dilution of 0.08% (FIG. 3A). Correlation coefficient of the standard curve was 0.998 with a slope value of −3.48 (FIG. 3B). Melting curve analysis revealed that the MYD88 L265P mutant-specific amplicon melted at 84° C. A minor non-specific amplification was only found in the dilution of 0.4% or lower with a melting peak at 80° C.
Figure 3B:
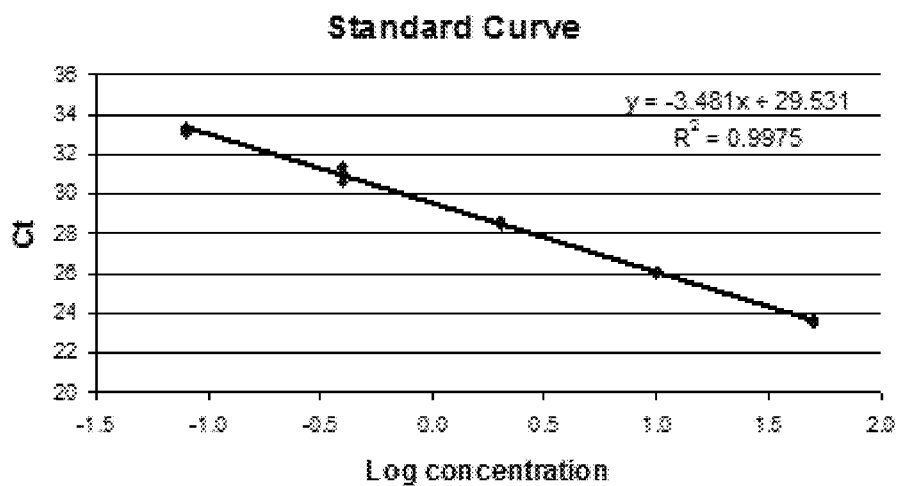
Figure 3C:
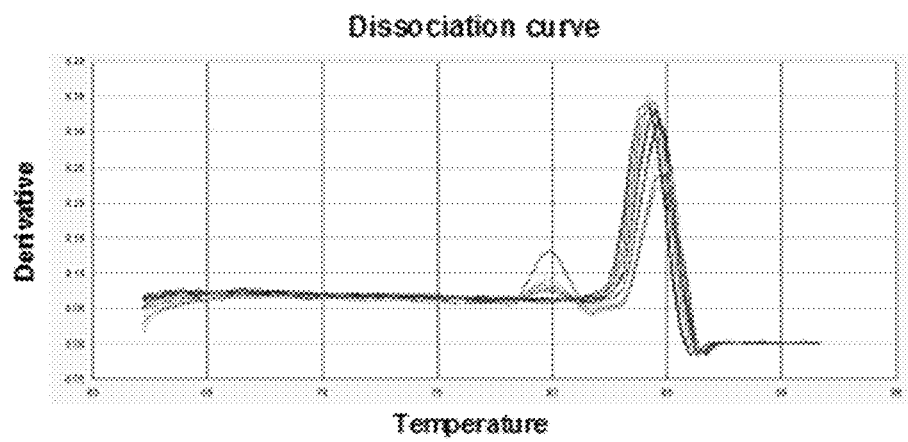

Next, a SYBR green-based real-time PCR was developed to allow quantification of MYD88 L265P. Given the high frequency of the MYD88 L265P mutation in WM, quantitative assessment of MYD88 L265P has potential to be developed as a robust biomarker for monitoring disease progression and response to treatment. Sensitivity and specificity of the real-time AS-PCR were determined by a serial dilution of the mutant DNA with the wild-type DNA. $C_T$ values were recorded for mutant-specific and reference PCR and the corresponding delta $C_T$ values were calculated. As shown in FIG. 3A, this real-time AS-PCR can detect the MYD88 L265P mutation at a dilution of 0.08% with more than 2 cycle differences from the wild-type DNA background. Correlation coefficient of the standard curve was 0.998 with a slope value of −3.5 (FIG. 3B). The melting curve analysis revealed that the MYD88 L265P mutant-specific amplicon melted at 840 C (FIG. 3C). A minor non-specific amplification was only found in the dilution of 0.4% or lower with a melting peak at 80° C.

Figure 3D:
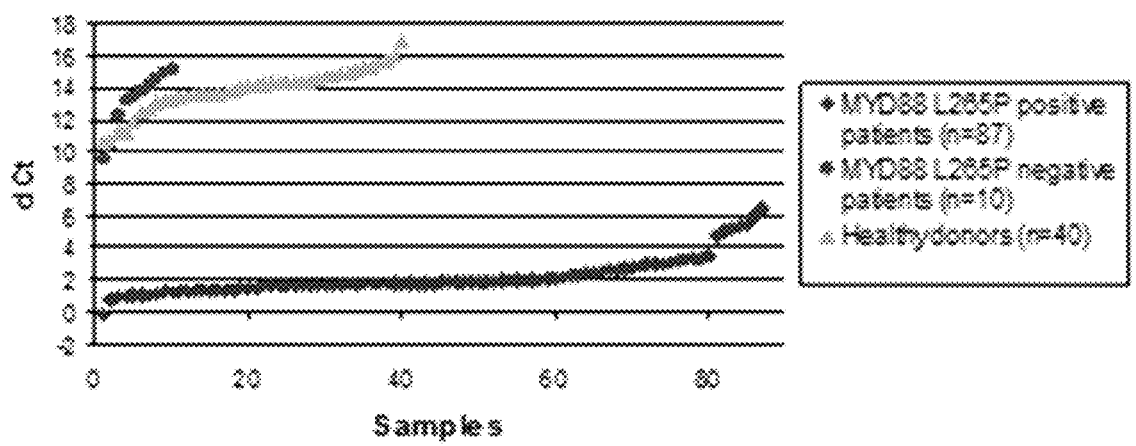

To gain more information on the performance of the assays, all samples that have been analyzed by the gel-based AS-PCR and Sanger sequencing were reanalyzed by the real-time AS-PCR. As shown in the scatter plot (FIG. 3D), the healthy donors (n=40) had delta CT values ranging from 10.7 to 16.9 cycles (mean, 13.9 cycles; median, 14.1 cycles), whereas the WM patients had delta CT values ranging from −0.2 to 15.2 cycles (mean, 3.3 cycles; median, 1.9 cycles). There were two major clusters of WM patients separated by 3.2 cycles. The cluster with delta CT values ranging from 9.6 to 15.2 cycles (n=10) looked similar to healthy donors. Thus, this cluster was determined as MYD88 L265P negative. By contrast, another cluster had delta CT values ranging from −0.2 to 6.4 cycles (n=87). This cluster was determined as MYD88 L265P positive. In addition, the gel-based AS-PCR and the real-time AS-PCR showed an exactly same result of determining the status of MYD88 L265P in this cohort. The overall results suggest that a small subset of WM patients may not carry the MYD88 L265P mutation. Furthermore, the entire coding region of the MYD88 gene was sequenced for the 10 patients who were negative for MYD88 L265P as determined by AS-PCR. No MYD88 mutation was found.

Correlation Between MYD88 L265P Mutation Status and Clinical Characteristics

MYD88 L265P was initially reported in DLBCL as a gain-of-function mutation that promotes NF-kB and JAK-STAT3 signaling through activating the IRAK family of serine-threonine kinases. Interestingly, MYD88 L265P was frequently mutated in the ABC subtype of DLBCL (29%) but rare in the GCB subtype. We sought to evaluate the differences of clinical characteristics between the two clusters of WM patients determined by AS-PCR. Non-parametric ANOVA analysis revealed that the MYD88 L265P positive patients tended to have greater BM involvement (p=0.001), lower serum IgG (p=0.011), and higher serum IgM (p=0.007) compared to the MYD88 L265P negative patients (Table 3). Due to small number of MYD88 L265P negative patients, the observations need to be confirmed in an independent study with large sample size.

Determination of Therapeutic Effect by Quantitative Assessments of MYD88 L265P

To explore the potential of using the real-time AS-PCR method to determine therapeutic effect and monitor residual disease in WM, concordance between the readouts of BM involvement and levels of mutant MYD88 L265P for seven patients who received pharmacological intervention and provided BM biopsies before and after treatment was examined. The results are summarized in Table 4. Patient A was a homozygous carrier of MYD88 L265P and had 70% BM involvement and high level of mutant MYD88 L265P before treatment. This patient exhibited a complete clinical remission after the treatment. Accordingly, the BM involvement and the levels of mutant MYD88 L265P became undetectable. Patient B and C showed approximately 90% decrease in the BM involvement with the treatments. Similarly, a marked decrease in the levels of mutant MYD88 L265P was also observed from the two patients (96% and 74%, respectively). Patient D showed 47% decrease in the BM involvement versus 45% decrease in the levels of mutant MYD88 L265P. However, the levels of mutant MYD88 L265P were little changed in patient E and F who showed 17% and 37% decreases in the BM involvement, respectively. The last patient (G) did not appear to respond to the treatment and showed slightly increase in both BM involvement and levels of mutant MYD88 L265P. Linear regression analysis revealed a high correlation between the percentage changes of BM involvement and levels of mutant MYD88 L265P (R2=0.90, p=0.001). Although the study sample size was very small, the results supported the hypothesis of using quantitative assessment of MYD88 L265P to determine therapeutic effect and monitor residual disease in WM.

BM Examination is Essential in the Clinical Staging of Non-Hodgkin's Lymphomas (NHLs)

Merli et al reported a comparison between histology and flow cytometry (FC) on the assessments of BM involvement in non-Hodgkin's lymphomas (NHLs) including LPL (Assessment of bone marrow involvement in non-Hodgkin's lymphomas: comparison between histology and flow cytometry, *Eur J Haematol*, 85(5):405-15, 2010). A high concordance between the two methods was observed for most NHLs. However, significant discordance was reported in LPL. It was speculated that FC may underestimate the extent of infiltrate with respect to histology. Quantitative assessment of MYD88 L265P in BM biopsy represents a novel tool contributing to clinical staging at diagnosis in WM.

In conclusion, a sensitive and inexpensive real-time AS-PCR method has been developed that permits reliable and quantitative assessments of MYD88 L265P. This is the first quantitative assay for MYD88 L265P and will facilitate testing the potential of MYD88 L265P as a biomarker to improve diagnosis and clinical staging and monitor disease progression and response to treatment in WM.

Example 3

Bruton's tyrosine kinase (BTK) promotes B-cell receptor signaling along with B-cell expansion and survival through NF-κB and MAPK. MYD88 L265P is a widely expressed somatic mutation in tumor cells from WM patients. MYD88 L265P promotes enhanced tumor cell survival through IRAK 1/4 mediated NF-κB and MAPK signaling. We therefore sought to clarify the role of BTK signaling in MYD88 L265P expressing WM cells, and the impact of BTK and MYD88/IRAK inhibition on WM cell signaling and survival.

Materials and Methods

Western blot analysis was performed using total and phospho-specific antibodies in MYD88 L265P expressing WM cells, BCWM.1 and MCWL-1 following MYD88 knockdown by lentiviral transduction, and/or use of MYD88 or IRAK signal inhibitors. Cells were also treated with the BTK inhibitor PCI-32765, in the presence or absence of MYD88 homodimerization or IRAK1/4 inhibitors. Annexin V/PI staining was used to assess cell survival, and synergism assessed with CalcuSyn software.

Results

Figure 4:
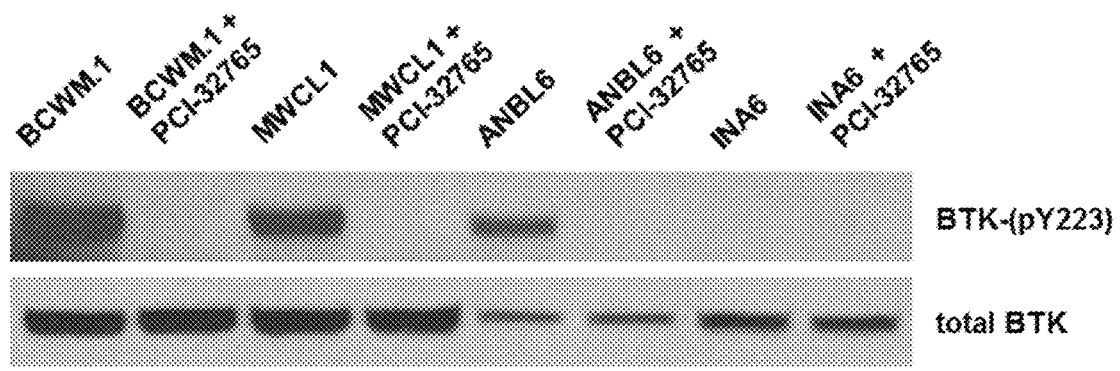
FIG. 4 shows increased phosphorylation of BTK by western blotting with phospho-specific antibody in Waldenstrom's Macroglobulinemia (WM) cell lines, BCWM.1 and MWCL-1, compared to Multiple myeloma cell lines, ANBL6 and INA6. Antibody against total BTK was used as loading control. PCI-32765 significantly blocked the BTK phosphorylation in WM cells.

BTK was highly expressed and phosphorylated in MYD88-L265P expressing WM cells and PCI-32765 significantly blocked the BTK activation (FIG. 4). Increased phosphorylation of BTK was confirmed by western blotting with phospho-specific antibody in Waldenstrom's Macroglobulinemia (WM) cell lines, BCWM.1 and MWCL-1, compared to Multiple myeloma cell lines, ANBL6 and INA6. Antibody against total BTK was used as loading control. PCI-32765 significantly blocked the BTK phosphorylation in WM cells.

Figure 5:
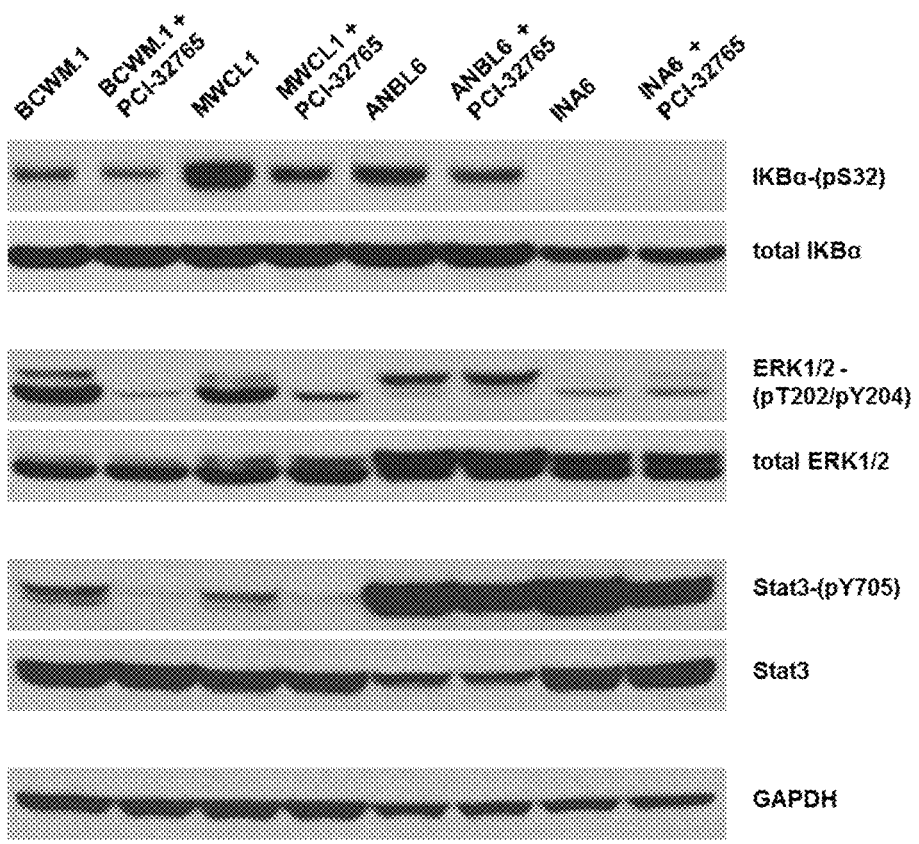
FIG. 5 shows that PCI-32765 blocked the downstream NF-kB, MAPK, Stat3 signaling by significantly reducing the phosphorylation of IKBα, ERK1/2 and Stat3 proteins in WM cell lines, BCWM.1 and MWCL-1, compared to multiple myeloma cell lines, ANBL6 and INA6. Antibodies against corresponding total proteins and GAPDH were used as loading controls.

PCI32765 significantly reduced downstream NF-kB, MAPK and STAT3 signaling in WM cells (FIG. 5). In addition to significantly blocking the BTK activation, PCI-32765 also blocked the downstream NF-kB, MAPK, Stat3 signaling by significantly reduced the phosphorylation of IKBα, ERK1/2 and Stat3 proteins in WM cell lines, BCWM.1 and MWCL-1, compared to multiple myeloma cell lines, ANBL6 and INA6. Antibodies against corresponding total proteins and GAPDH were used as loading controls.

Figure 6:
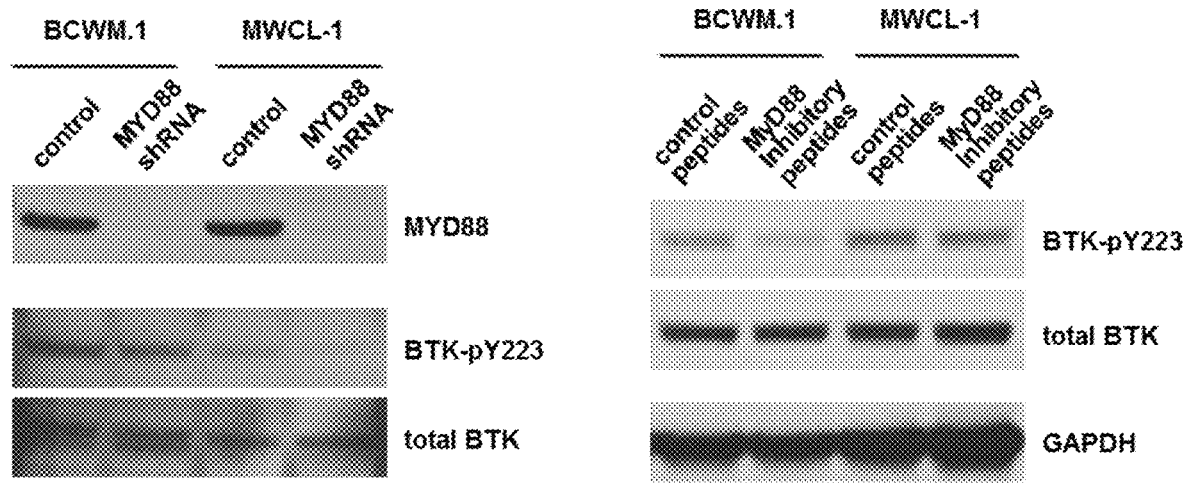
FIG. 6 shows that knockdown of MYD88 by lentiviral transduction, and/or use of a MYD88 inhibitor leads to decreased BTK phosphorylation. Antibodies against total BTK and/or GAPDH were used as loading control.

Knockdown of MYD88 by lentiviral transduction, and/or use of a MYD88 inhibitor leads to decreased BTK phosphorylation (FIG. 6). MYD88 knockdown was confirmed by western blot in BCWM.1 and MWCL-1 cells. The knockdown of MYD88 reduced BTK phosphorylation compared with controls. MYD88 homodimerization inhibitory peptides significantly reduced BTK phosphorylation compared with control peptides. Antibodies against total BTK and/or GAPDH were used as loading control.

Figure 7A:
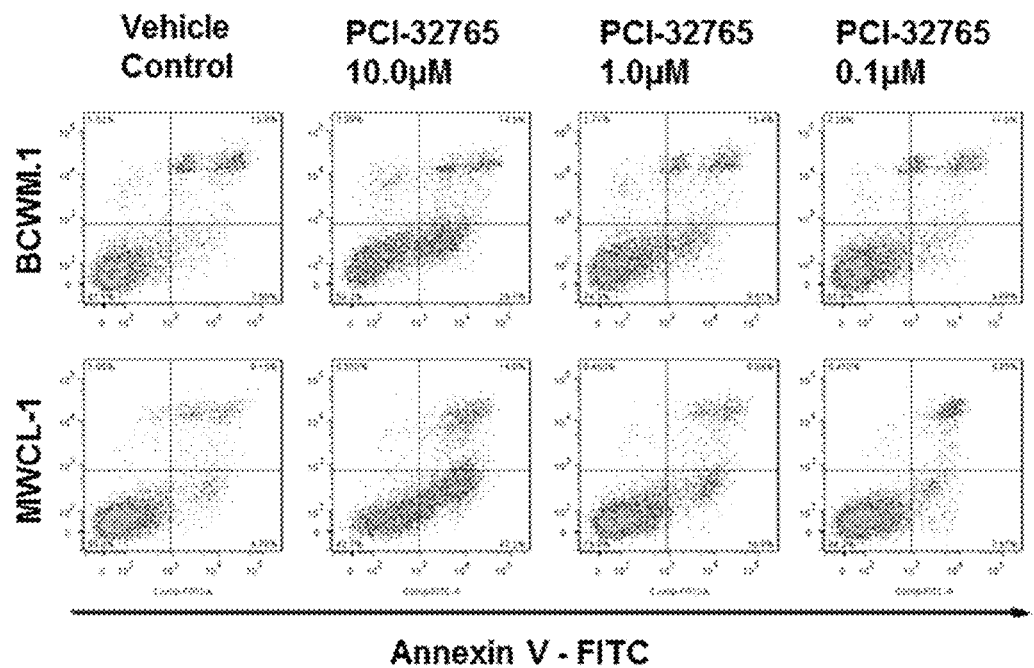
FIGS. 7A-7C demonstrate that BTK inhibitor PCI-32765 induces apoptosis of MYD88 L265P expressing WM cells alone and in combination with MYD88 pathway inhibitor and IRAK 1/4 kinase inhibitor. Apoptosis analysis was performed using Annexin V and PI staining after PCI-32765 treatment for 24 hrs (FIG. 7A).
Figure 7B:
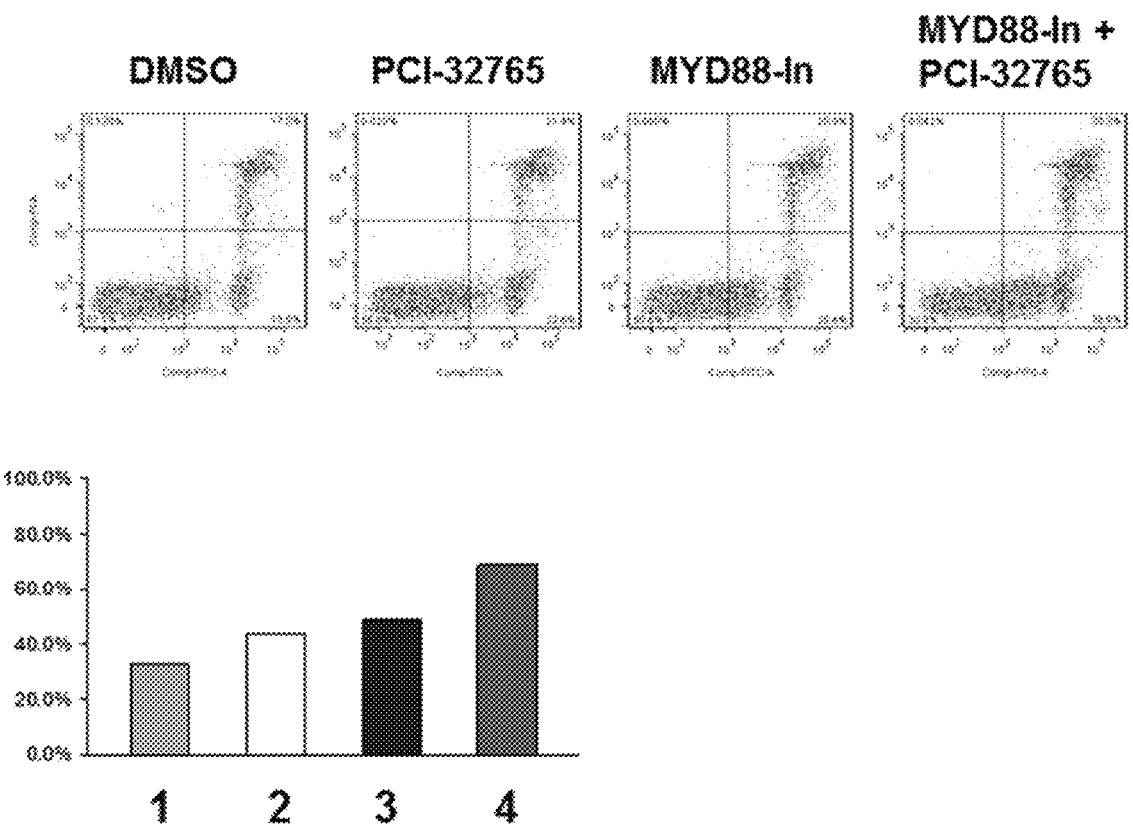
Figure 7C:
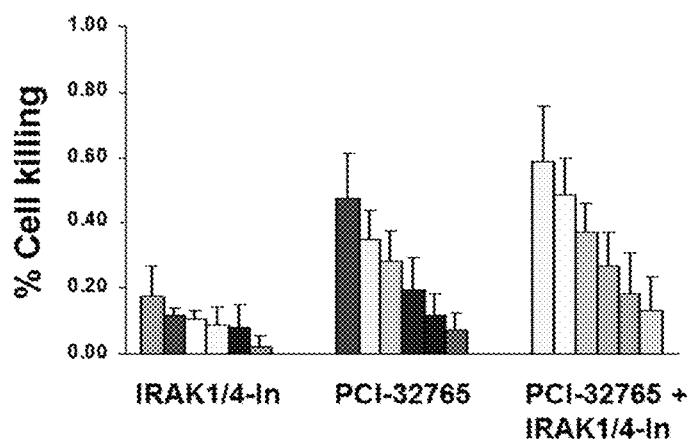
Figure 7C:
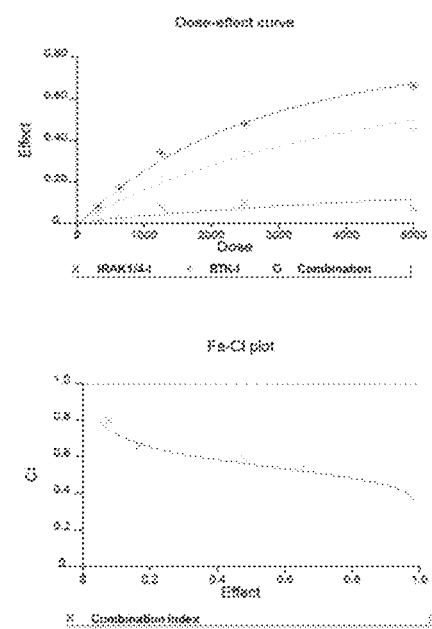

Treatment with PCI-32765 induces apoptosis of MYD88 L265P expressing WM cells (FIG. 7A). PCI-32765 shows robust tumor cell killing in combination with a MYD88 pathway inhibitor in primary WM patients bone marrow tumor cells (FIG. 7B). PCI-32765 shows synergistic tumor cell killing in combination with an IRAK 1/4 kinase inhibitor (FIG. 7C).

BTK activation is facilitated by MYD88 pathway signaling in MYD88 L265P expressing WM cells, and participates in MYD88 downstream signaling. Inhibition of BTK by PCI-32765 leads to robust tumor killing of MYD88 L265P expressing WM cells, which is potentiated by MYD88 pathway inhibitors.

REFERENCES

1. Owen R G, Treon S P, Al-Katib A, et al. Clinicopathological definition of Waldenstrom's macroglobulinemia: Consensus panel recommendations from the Second International Workshop on Waldenstrom's Macroglobulinemia. Semin Oncol. 2003; 30(2):110-115.
2. Swerdlow, SH, Campo, E, Harris, N L, et al. (eds). World Health Organization Classification of Tumours of Haematopoietic and Lymphoid Tissues (4th edition). Lyon, France. IARC Press, 2008:194-5.
3. Treon S P, Hunter Z R, Aggarwal A, et al. Characterization of familial Waldenstrom's macroglobulinemia. Ann Oncol. 2006; 17(3):488-494.
4. McMaster M L, Csako G, Giambarresi T R, et al. Long-term evaluation of three multiple-case Waldenstrom macroglobulinemia families. Clin Cancer Res. 2007; 13(17):5063-9.
5. Kyle R A, Benson J, Larson D R, Therneau $T_M$, Dispenzieri A, Melton L J, Rajkumar S V. IgM monoclonal gammopathy of undetermined significance and smoldering Waldenstrom's Macroglobulinemia. Clin Lymphoma Myeloma. 2009; 9(1):17-18.
6. Roach J C, Glusman G, Smit A F A, et al. Analysis of genetic inheritance in a family quartet by whole-genome sequencing. Science. 2010; 328(5978): 636-9.
7. Lee W, Jiang Z, Liu J, et al. The mutation spectrum revealed by paired genome sequences from a lung cancer patient. Nature. 2010; 465(7297): 473-77.
8. Drmanac R, Sparks A B, Callow M J, et al. Human genome sequencing using unchained base reads on self-assembly DNA nanoarrays. Science. 2010; 327(5961): 78-81.
9. CGATools Methods. http://cgatools.sourceforge.net/docs/1.3.0/cgatools-methods.pdf, pages 12-16.
10. Carnevali P, Baccash J, Halpern A L, et al. Techniques for Human Genome Resequencing Using Mated Gapped Reads. Manuscript submitted.
11. Watters T, Kenny E F, O'Neill L A J. Structure, function and regulation of the Toll/IL-1 receptor adaptor proteins. Immunol Cell Biol. 2007; 85(6): 411-419.
12. Loiarro M, Gallo G, Fanto N, et al. Identification of critical residues of the MYD88 death domain involved in the recruitment of downstream kinases. J Biol Chem. 2009; 284(41): 28093-281023.
13. Lin S C, Lo Y C, Wu H. Helical assembly in the MYD88-IRAK4-IRAK2 complex in TLR/IL-1R signaling. Nature. 2010; 465(7300): 885-891.
14. Kawagoe T, Sato S, Matsushita K, et al. Sequential control of Toll-like receptor dependent responses by IRAK1 and IRAK2. Nature Immunol. 2008; 9(6):684-691.
15. Brikos C, Wait R, Begum S, et al. Mass spectrometric analysis of the endogenous type 1 interleukin-1 (IL-1) receptor signaling complex formed after IL-1 binding indetifies IL-1RAcP, MYD88, and IRAK-1 as the stable components. Mol Cell Proteomics. 2007; 6(9): 1551-1559.
16. Ngo V N, Young R M, Schmitz R, et al. Oncogenically active MYD88 mutations in human lymphoma. Nature. 2011; 470(7332): 115-121.
17. Loiarro M, Sette C, Gallo C, et al. Peptide mediated interference of TIR domain dimerization in MYD88 inhibits Il-1 dependent activation of NF-kB. J Biol Chem 1994; 269:10444-50.
18. Powers J P, Li S, Jaen J C, Liu J, Walker N P, Wang Z, Wesche H. Discovery and initial SAR of inhibitors of interleukin-1 receptor-associated kinase-4. Bioorg Med Chem Lett. 2006; 16(11):2842-5.
19. Leleu X, Eeckhoute J, Jia X, et al. Targeting N F-kappaB in Waldenstrom macroglobulinemia. Blood. 2008; 111 (10): 5068-77.

TABLE 1

Clinical and laboratory characteristics for 30 WM patients whose lymphoplasmacytic cells were used in whole genome sequencing studies.

|  | Median | Range |
|---|---|---|
| Age | 62 | 41-87 |
| Familial WM | 9 (30%) | NA |
| Untreated | 26 (87%) | NA |
| Bone Marrow Involvement (%) | 65% | 5-95% |
| Clonal B-cells(%)[1] | 96.3 | 55.5-100 |
| IgM (mg/dL) | 3,970 | 590-6,580 |
| IgMκ/IgMλ monoclonal protein | 24/6 | NA |
| IgA (mg/dL) | 41 | 11-516 |
| IgG (mg/dL) | 519 | 215-3,120 |
| Serum B$_2$M (mg/L) | 3.55 | 1.50-12.1 |
| Hematocrit (%) | 31.4 | 24.0-41.5 |

[1]Determined by light chain restriction using flow cytometry.

TABLE 2

Clinical and laboratory characteristics for the 8 IgM MGUS patients who underwent Sanger sequencing for the MYD88 L265P variant.

|  | Median | Range |
|---|---|---|
| Age | 62 | 52-71 |
| Familial WM | 2 (25%) | NA |
| Untreated | 8 (100%) | NA |
| Bone Marrow Involvement (%) | 0% | 0-2% |
| Clonal B-cells(%)[1] | 0% | 0-1 |
| IgM (mg/dL) | 682 | 142-1,190 |
| IgMκ/IgMλ monoclonal protein | 5/3 | NA |
| IgA (mg/dL) | 142 | 53-244 |
| IgG (mg/dL) | 772 | 523-1,040 |
| Serum B$_2$M (mg/L) | 1.70 | 1.30-2.10 |
| Hematocrit (%) | 41.4 | 36.7-44.8 |

[1]Determined by light chain restriction using flow cytometry.

TABLE 3

Correlation between MYD88 L265P mutation status and clinical characteristics

| Clinical parameter | MYD88 L265P mutation status Positive | | MYD88 L265P mutation status Negative | | p-value* |
|---|---|---|---|---|---|
| Age at diagnosis | n = 87 | 60.26 (9.97) | n = 10 | 66.50 (8.33) | 0.064 |
| Gender, % female | n = 86 | 40.91% | n = 10 | 50.00% | 0.738** |
| Bone marrow involvement, % | n = 85 | 52.92 (30.49) | n = 10 | 18.00 (18.74) | 0.001 |
| IgA, mg/dL | n = 85 | 622.79 (552.45) | n = 10 | 970.10 (711.69) | 0.106 |
| IgG, mg/dL | n = 85 | 216.35 (322.36) | n = 10 | 332.10 (284.60) | 0.011 |
| IgM, mg/dL | n = 85 | 3093.62 (1943.89) | n = 10 | 1536.20 (2039.79) | 0.007 |

Values are mean (SD).
*Non-parametric ANOVA
**Fisher's exact test

TABLE 4

Concordance between the assessments of BM involvement and MYD88 L265P mutation levels.

| Patient | Age at diagnosis | Gender | Treatment status | BM Involvement (%) | Levels of mutant MYD88 L265P (%)* | % change of BM involvement | % change of MYD88 L265P levels |
|---|---|---|---|---|---|---|---|
| A** | 61 | Male | Untreated | 70 | 156.90 | 100 | 100 |
|  |  |  | Bendamustine rituxan | Negative | Negative |  |  |
| B | 44 | Male | Untreated | 90 | 60.73 | 89 | 96.33 |
|  |  |  | R-CD | 10 | 2.23 |  |  |
| C | 52 | Male | Untreated | 50 | 78.12 | 90 | 73.61 |
|  |  |  | R-CD | 5 | 19.08 |  |  |
| D | 59 | Male | Untreated | 95 | 99.15 | 47 | 45.39 |
|  |  |  | Everolimus | 50 | 54.15 |  |  |
| E | 63 | Male | Untreated | 90 | 96.07 | 17 | 1.14 |
|  |  |  | Everolimus | 75 | 94.97 |  |  |
| F | 70 | Male | Untreated | 95 | 95.93 | 37 | 8.61 |
|  |  |  | Everolimus | 60 | 87.67 |  |  |
| G | 63 | Male | Untreated | 20 | 67.93 | −25 | −12.87 |
|  |  |  | Everolimus | 25 | 76.67 |  |  |

R-CD: combination of rituximab, cyclophosphamide, and dexamethasone.
BM biopsy was collected before and after treatment. % of mutation was calculated based on standard curve.
**Homozygous carrier of the MYD88 L265P mutation.

I claim:

1. A method to treat lymphoplasmacytic lymphoma in a subject, the method comprising:
    selecting the subject with lymphoplasmacytic lymphoma on the basis that the subject has a mutation at position 38182641 in chromosome 3p22.2 in a biological sample from the subject,
    administering to the subject with lymphoplasmacytic lymphoma a myeloid differentiation primary response 88 (MYD88) inhibitor, an interleukin receptor associate kinase 1/4 (IRAK-1/4) inhibitor, and/or a Bruton's tyrosine kinase (BTK) inhibitor in an amount effective to treat lymphoplasmacytic lymphoma.

2. The method of claim 1, wherein the biological sample is a sample of bone marrow, lymph node, spleen or blood.

3. The method of claim 1, wherein the mutation results in a single nucleotide change from T to C in the myeloid differentiation primary response 88 (MYD88) gene.

4. The method of claim 1, wherein the mutation results in an amino acid change from leucine to proline at position 265 in the myeloid differentiation primary response 88 protein.

5. The method of claim 1, wherein the MYD88 inhibitor is a peptidomimetic compound ST2825.

6. The method of claim 1, wherein the IRAK-1/4 inhibitor is N-(2-Morpholinylethyl)-2-(3-nitrobenzoylamido)-benzimidazole.

7. The method of claim 1, wherein the BTK inhibitor is Ibrutinib (PCI-32765).

8. A method for monitoring progression or recurrence of lymphoplasmacytic lymphoma (LPL) in a subject and treating the subject, comprising
    obtaining multiple biological samples of the subject with lymphoplasmacytic lymphoma over a period of time,
    determining from the multiple biological samples the level of a transcript comprising a mutation at position 38182641 in chromosome 3p22.2,
    and administration of an effective amount of a myeloid differentiation primary response 88 (MYD88) inhibitor, an interleukin receptor associate kinase 1/4 (IRAK-1/4) inhibitor, and/or a Bruton's tyrosine kinase (BTK) inhibitor to the subject when a change in the level of the transcript over the period of time is indicative of the progression or recurrence of LPL in the subject.

9. The method of claim 8, wherein the subject is undergoing chemotherapy.

10. The method of claim 8, wherein the level of the transcript is measured using quantitative real time polymerase chain reaction.

11. The method of claim 10, wherein the quantitative real time polymerase chain reaction is performed using an allele specific primer, wherein the allele specific primer hybridizes at or near its 3' end to the mutation at position 38182641 in chromosome 3p22.2.

12. The method of claim 11, wherein the allele specific primer is SEQ ID NO: 5.

13. The method of claim 8, wherein the biological sample is a sample of bone marrow, lymph node, spleen or blood.

14. The method of claim 8, wherein the mutation results in a single nucleotide change from T to C in the myeloid differentiation primary response 88 (MYD88) gene.

15. The method of claim 8, wherein the mutation results in an amino acid change from leucine to proline at position 265 in the myeloid differentiation primary response 88 protein.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 1
gggatatgct gaactaagtt gccac                                          25

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 2
gacgtgtctg tgaagttggc atctc                                          25

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3
gctgttgtta accctggggt tgaag                                          25

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 4
gacgtgtctg tgaagttggc atctc                                          25

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
ccttgtactt gatggggaac g                                              21

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
gccttgtact tgatggggaa ca                                             22

<210> SEQ ID NO 7
<211> LENGTH: 22
<212> TYPE: DNA
<213> ORGANISM: Artificial sequence

```
<220> FEATURE:
<223> OTHER INFORMATION: Synthetic oligonucleotide

<400> SEQUENCE: 7
aatgtgtgcc aggggtactt ag                                              22

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
tggtgtagtc gcagacagtg a                                               21

<210> SEQ ID NO 9
<211> LENGTH: 163
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (139)..(139)
<223> OTHER INFORMATION: n is T or C

<400> SEQUENCE: 9
gaatgtgtgc caggggtact tagatggggg atggctgttg ttaaccctgg ggttgaagac      60
tgggcttgtc ccaccatggg gcaagggcct gatgccagca tggcacccct tggcttgcag    120
gtgcccatca gaagcgacng atccccatca agtacaaggc aat                      163
```